(12) United States Patent
Banning et al.

(10) Patent No.: US 8,328,923 B2
(45) Date of Patent: *Dec. 11, 2012

(54) COMPOUNDS SUITABLE FOR USE IN INKS AND INKS HAVING SUCH COMPOUNDS

(75) Inventors: Jeffrey H. Banning, Hillsboro, OR (US); Stephan V. Drappel, Mississauga (CA); Michael B. Meinhardt, Mountain Circle, OR (US); Randall R. Bridgeman, Tualatin, OR (US); Alex J. Kugel, Fargo, ND (US)

(73) Assignee: Xerox Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/987,749

(22) Filed: Jan. 10, 2011

(65) Prior Publication Data

US 2011/0100254 A1    May 5, 2011

Related U.S. Application Data

(62) Division of application No. 12/044,514, filed on Mar. 7, 2008.

(51) Int. Cl.
*C09D 11/02* (2006.01)
(52) U.S. Cl. ............... 106/31.29; 106/31.75; 106/31.13
(58) Field of Classification Search .................. None
See application file for complete search history.

(56) References Cited

U.S. PATENT DOCUMENTS

| | | | |
|---|---|---|---|
| 2,382,919 A | 8/1945 | Sartori | |
| 5,424,767 A | 6/1995 | Alavizadeh et al. | |
| 5,782,966 A | 7/1998 | Bui et al. | |
| 5,902,841 A * | 5/1999 | Jaeger et al. | 523/161 |
| 5,919,839 A | 7/1999 | Titterington et al. | |
| 6,174,937 B1 | 1/2001 | Banning et al. | |
| 6,309,453 B1 | 10/2001 | Banning et al. | |
| 6,395,811 B1 | 5/2002 | Nguyen et al. | |
| 6,472,523 B1 | 10/2002 | Banning et al. | |
| 6,713,614 B2 | 3/2004 | Carlini et al. | |
| 6,946,025 B2 | 9/2005 | Wu et al. | |
| 6,958,406 B2 | 10/2005 | Banning et al. | |
| 6,998,493 B2 | 2/2006 | Banning et al. | |
| 7,144,450 B2 | 12/2006 | Goredema et al. | |
| 7,153,349 B2 | 12/2006 | Carlini et al. | |
| 7,211,131 B2 | 5/2007 | Banning et al. | |
| 7,294,730 B2 | 11/2007 | Banning et al. | |
| 7,314,949 B2 | 1/2008 | Goredema et al. | |
| 7,317,122 B2 | 1/2008 | Carlini et al. | |
| 2002/0150602 A1 | 10/2002 | Livoreil et al. | |
| 2005/0090690 A1 | 4/2005 | Wu et al. | |

FOREIGN PATENT DOCUMENTS

| | | |
|---|---|---|
| CA | 2488086 | 5/2005 |
| EP | 1 149 880 A1 | 10/2001 |
| EP | 1 174 110 A1 | 1/2002 |
| EP | 1 177 784 A2 | 2/2002 |
| JP | 03-11361 A | 1/1991 |
| JP | 08-048965 | 2/1996 |
| JP | 10-237034 A | 9/1998 |
| JP | 2000-144025 A | 5/2000 |
| JP | 2003-247195 A | 9/2003 |
| JP | 2005-255821 A | 9/2005 |
| JP | 2005-330309 A | 12/2005 |
| JP | 2006-100130 A | 4/2006 |
| WO | WO 2004/106442 A2 | 12/2004 |

OTHER PUBLICATIONS

Bertsch et al. (Fette, Seifen, Anstrichmittel, vol. 68(10), pp. 817-824, 1966, and an English translated Abstract cited from SciFinder.*
Zoretic et al. (J. Med. Chem., 1978, vol. 21, No. 12, 1330-2.*
Sedavkina et al. (Fiz.-Khim. Issled. Obl. Org. Nek. Neorg. Soedin. pp. 8-11, conference, 1974, and also see attached an English translated Abstract cited from SciFinder.*
Notice of Allowance mailed Aug. 9, 2011 in pending U.S. Appl. No. 12/948,524.
Office Action mailed May 25, 2011 in pending U.S. Appl. No. 12/948,546.
Mack et al., "Hydroxystearic Acids. I. The Catalytic Hydrogenation of the 9, 10-Epoxystearates", pp. 686-692, Nov. 24, 1952.
Canadian Office Action issued May 9, 2011 in Canadian Patent Application No. 2,656,505.
Notice of Allowance mailed Jun. 27, 2011 in pending U.S. Appl. No. 12/948,546.
Office Action mailed Jun. 24, 2011 in pending U.S. Appl. No. 12/948,524.
Notice of Allowance mailed Mar. 15, 2011 in pending U.S. Appl. No. 12/948,551.
Office Action mailed Mar. 24, 2011 in pending U.S. Appl. No. 12/948,524.
European Office Action issued May 31, 2010 in European Patent Application No. 09152498.3.
D. F. Jones et al., "Microbiological Oxidation of Long-chain Aliphatic Compounds. Part IV. Alkane Derivatives Having Polar Terminal Groups", Journal of the Chemical Society, 1968, pp. 2822-2827.
Fumihiko Yoshizaki et al., "Intramolecular Effect of 1-($\omega$-hydroxyalkyl) Groups on Alkali Degradation of 3-methyl-1-($\omega$-hydroxyalkyl)uracils", Heterocycles, vol. 3, No. 10, (1975), pp. 827-831.
Phillip A. Zoretic et al., "Synthesis and Gastric Antisecretory Properties of an 8-Aza- and a 10-Oxa-8,12-secoprostaglandin", Journal of Medicinal Chemistry, vol. 21, No. 12, (1978), pp. 1330-1332.
Sunil V. Pansare et al., "Enantioselective Synthesis of $\alpha$-hydroxy $\gamma$-butyrolactones From an Ephedrine-derived Morpholine-dione", Tetrahedron 58 (2002), pp. 8985-8991.
Office Action mailed Feb. 17, 2011 in pending U.S. Appl. No. 12/948,546.
Office Action mailed Feb. 17, 2011 in pending U.S. Appl. No. 12/948,551.
Office Action mailed Jan. 17, 2012 in U.S. Appl. No. 12/948,532.

\* cited by examiner

*Primary Examiner* — Melvin C Mayes
*Assistant Examiner* — Yun Qian
(74) *Attorney, Agent, or Firm* — Oliff & Berridge, PLC

(57) ABSTRACT

Disclosed herein are ink compositions including an ink vehicle and a colorant, wherein the ink vehicle includes a compound having a formula of $R^1$—CONH—$R^2$ or $R^2$—CONH—$R^1$, wherein $R^2$ is an alkyl group having from 1 to about 18 carbon atoms and $R^1$ is an alkyl group having from about 3 carbon atoms to about 200 carbon atoms, wherein $R^2$ and $R^1$ have the same number of carbon atoms or $R^2$ has less carbon atoms than $R^1$, and wherein at least one of the alkyl groups for $R^2$ and $R^1$ includes at least one hydroxyl group substituent.

16 Claims, No Drawings

COMPOUNDS SUITABLE FOR USE IN INKS AND INKS HAVING SUCH COMPOUNDS

CROSS-REFERENCE TO RELATED APPLICATION

This application is a divisional application of U.S. patent application Ser. No. 12/044,514, filed Mar. 7, 2008, the entire disclosure of which is incorporated herein by reference.

BACKGROUND

Described herein are amide compounds suitable for use in various inks. The amide compounds described herein may be particularly useful as substitutes for various known ink vehicles or as supplements to various known ink vehicles.

Ink jetting devices are well known in the art. Ink jet printing systems are generally of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium. There are generally three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. As is known, an acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. Still another type of drop-on-demand system is known as thermal ink jet, or bubble jet, and produces high velocity droplets. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink vehicle (usually water) in the immediate vicinity to vaporize almost instantaneously and create a bubble. The ink at the orifice is forced out as a propelled droplet as the bubble expands.

Ink jet printing processes may employ inks that are solid at room temperature and liquid at elevated temperatures. Such inks may be referred to as hot melt inks or phase change inks. In thermal ink jet printing processes employing hot melt inks, the solid ink is melted by the heater in the printing apparatus and utilized (for example, jetted) as a liquid in a manner similar to that of conventional thermal ink jet printing. Upon contact with the printing substrate, the molten ink solidifies rapidly, enabling the colorant to substantially remain on the surface of the substrate instead of being carried into the substrate (for example, paper) by capillary action, thereby enabling higher print density than is generally obtained with liquid inks.

When the amide compounds described herein are utilized in the ink vehicle of a phase change ink, such amide compounds have the ability to use fewer components in the ink vehicle, thereby reducing cost and allowing the ink to be more uniform.

SUMMARY

Disclosed herein is an ink composition comprising an ink vehicle and a colorant, wherein the ink vehicle comprises a compound having a formula of $R^1$—CONH—$R^2$ or $R^2$—CONH—$R^1$, wherein $R^2$ is an alkyl group having from 1 to about 18 carbon atoms and $R^1$ is an alkyl group having from about 3 carbon atoms to about 200 carbon atoms, wherein $R^2$ and $R^1$ have the same number of carbon atoms or $R^2$ has less carbon atoms than $R^1$, and wherein at least one of the alkyl groups for $R^2$ and $R^1$ includes at least one hydroxyl group substituent.

Further disclosed is a phase change ink composition comprising an ink vehicle and a colorant, wherein the phase change ink is solid at temperatures of from about 20° C. to about 27° C. and exhibits a viscosity of from about 1 to about 20 centipoise (cP) at an elevated temperature at which the phase change ink is to be jetted, wherein the ink vehicle comprises a compound having a formula of $R^1$—CONH—$R^2$ or $R^2$—CONH—$R^1$, wherein $R^2$ is an alkyl group having from 1 to about 18 carbon atoms and $R^1$ is an alkyl group having from about 3 carbon atoms to about 200 carbon atoms, wherein $R^2$ and $R^1$ have the same number of carbon atoms or $R^2$ has less carbon atoms than $R^1$, and wherein at least one of the alkyl groups for $R^2$ and $R^1$ includes at least one hydroxyl group substituent.

EMBODIMENTS

The phase change inks herein include an ink vehicle that is solid at temperatures of from about 20° C. to about 27° C., for example room temperature, and specifically are solid at temperatures below about 40° C. However, the inks change phase upon heating, and are in a molten state at jetting temperatures. Thus, the inks have a viscosity of from about 1 to about 20 centipoise (cP), such as from about 5 to about 15 cP or from about 8 to about 12 cP, at an elevated temperature suitable for ink jet printing, such as temperatures of from about 50° C. to about 150° C., such as from about 70° C. to about 130° C. or from about 80° C. to about 120° C.

In one embodiment, the ink compositions have melting points of no lower than about 40° C., in another embodiment of no lower than about 60° C., and in yet another embodiment of no lower than about 80° C., and have melting points in one embodiment of no higher than about 160° C., in another embodiment of no higher than about 140° C., and in yet another embodiment of no higher than about 100° C., although the melting point can be outside of these ranges. The ink compositions disclosed herein generally have melt viscosities at the jetting temperature, in one embodiment no lower than about 75° C., in another embodiment no lower than about 100° C., and in yet another embodiment no lower than about 120° C., and in one embodiment no higher than about 180° C., and in another embodiment no higher than about 150° C., although the jetting temperature can be outside of these ranges, in one embodiment of no more than about 30 centipoise, in another embodiment of no more than about 20 centipoise, and in yet another embodiment of no more than about 15 centipoise, and in one embodiment of no less than about 2 centipoise, in another embodiment of no less than about 5 centipoise, and in yet another embodiment of no less than about 7 centipoise, although the melt viscosity can be outside of these ranges.

Disclosed herein are amide compounds suitable for use in phase change, low energy ink vehicles.

Alkyl Amides

In a first embodiment, the ink vehicle compound is a compound having a formula of $R^1$—CONH—$R^2$ or a formula of $R^2$—CONH—$R^1$, wherein $R^2$ is alkyl group having from 1 to about 18 carbon atoms and $R^1$ is a straight chain or branched alkyl group having from about 3 carbon atoms to about 200 carbon atoms, and wherein $R^2$ and $R^1$ have the same number of carbon atoms or $R^2$ has less carbon atoms than $R^1$.

$R^2$ may be an alkyl group having from 1 to about 18 carbon atoms, such as from 1 to about 15 carbon atoms or from 1 to about 10 carbon atoms. $R^2$ may be a linear, branched, saturated, unsaturated, substituted, or unsubstituted alkyl group, and wherein heteroatoms such as oxygen, nitrogen, sulfur, silicon, phosphorus, boron, and the like either may or may not be present as substitutions in the alkyl group. Further, $R^2$ may include any suitable substituents, such as hydroxy groups, halogen atoms, amine groups, imine groups, ammonium groups, azo groups, cyano groups, pyridine groups, pyridinium groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like. For example, $R^2$ may be an alkyl group selected from methyl, ethyl, n-propyl, isopropyl, n-butyl, isobutyl, sec-butyl, t-butyl, n-pentyl, 2-pentyl, 3-pentyl, t-pentyl, neopentyl, hexyl (including all isomers), heptyl (including all isomers), octyl (including all isomers), nonyl (including all isomers), decyl (including all isomers), undecyl (including all isomers), dodecyl (including all isomers), tridecyl (including all isomers), tetradecyl (including all isomers), pentadecyl (including all isomers), hexadecyl (including all isomers), heptadecyl (including all isomers) and octadecyl (including all isomers).

In embodiments, $R^1$ is a straight chain or branched chain alkyl group having from about 3 carbon atoms to about 200 carbon atoms, such as from about 5 carbon atoms to about 150 carbon atoms or from about 15 carbon atoms to about 100 carbon atoms. In embodiments, the straight chain or branched alkyl group of $R^1$ may have hydroxyl substitutions and optional heteroatoms, where suitable. However, in an embodiment, if $R^1$ is a straight chain alkyl group having no hydroxyl substituents, it is then desirable that no other substitutions and no heteroatoms be present.

Specifically, in embodiments, $R^2$ is $CH_3$ and the compound will have a formula of

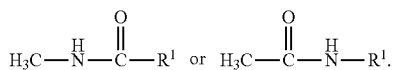

The alkyl amide compound having a formula of $R^1$—CONH—$R^2$ or $R^2$—CONH—$R^1$ may be derived by reacting a sufficient amount of an alkyl amine with a sufficient amount of a straight chain carboxylic acid or a branched carboxylic acid to ensure that the alkyl amide compound of the present embodiment is obtained. This reaction occurs at a temperature in a range of from about 80° C. to about 220° C., such as from about 85° C. to about 215° C. or from about 90° C. to about 180° C. The straight chain or branched carboxylic acid may optionally include hydroxyl substituents or heteroatoms depending upon the desired alkyl amide. In embodiments, the compound having a formula of $R^1$—CONH—$R^2$ may be obtained by, for example, reacting $R^1$—$CO_2H$ and $H_2N$—$R^2$.

The alkyl amide compound having a formula of $R^1$—CONH—$R^2$ or $R^2$—CONH—$R^1$ may be utilized as an ink vehicle in a solid phase change ink because its melting characteristics are suitable for use in phase change inks. The compound when $R^1$ has no hydroxyl group substituents exhibits both a crystalline and an amorphous portion. Specifically, the portion of the compound derived from the straight-chain carboxylic acid, that is derived from $R^1$, is crystalline, which decreases viscosity; however, the portion of the compound derived from the alkyl amine, that is derived from $R^2$, is amorphous, which improves hardness. Thus, the alkyl amide compound having a formula of $R^1$—CONH—$R^2$ or $R^2$—CONH—$R^1$, when $R^1$ has no hydroxyl group substituents, can exhibit both improved viscosity and hardness compared to phase change inks not having the alkyl amide compound of formula $R^1$—CONH—$R^2$ or $R^2$—CONH—$R^1$ described herein.

When the alkyl amide compound disclosed herein is derived from straight-chain carboxylic acids, the alkyl amide compound may be a highly crystalline material with viscosities of from about 0.01 cps to about 25 cps, such as from about 0.1 cps to about 15 cps or from about 1 cps to about 10 cps at about 140° C. The heat of fusion of an alkyl amide compound derived from a straight chain carboxylic acid may be of greater than about 100 J/g, such as greater than 125 J/g or greater than 150 J/g, as measured by a Differential Scanning calorimeter Q1000 made by TA Instruments at a constant heating and cooling rate of about 10° C./min. The hardness of such alkyl amide compounds as measured with a Koehler K95500 Digital Penetrometer according to ASTM D1321 is from about 0.01 dmm (decimillimeters) to about 75 dmm, such as from about 0.1 dmm to about 50 dmm or from about 0.5 dmm to about 25 dmm.

Alkyl amide compounds having a hydroxyl functionality, that is derived from, for example, hydroxystearic acid or aleuritic acid, are solid with viscosities of from about 100 cps to about 5000 cps, such as from about 100 cps to about 1000 cps or from about 100 cps to about 500 cps at a temperature of about 140° C.

Alkyl amide compounds derived from branched acids may be liquid or solid at room temperature. For example, an alkyl amide compound derived from, for example, isostearic acid or 2-ethylhexanoic acids, may be liquid at room temperature, that is, approximately 25° C., with a viscosity of from about 0.01 cps to about 25 cps, such as from about 0.1 cps to about 15 cps or from about 1 cps to about 10 cps. In alternative examples, an alkyl amide compound derived from, for example, Isocarb 24 acid, may be solid at room temperature, that is, approximately 25° C., with viscosities of from about 100 cps to about 5000 cps, such as from about 100 cps to about 1000 cps or from about 100 cps to about 500 cps.

The alkyl amides described herein may be utilized in known ink formulations in addition to the known ink vehicles or as a replacement for a portion of the ink vehicle. For example, alkyl amides derived from straight chained or branched carboxylic acid having at least one hydroxyl substituent could replace or supplement rosin esters in known ink formulations while straight chained alkyl amides derived from straight chained or branched carboxylic acid not having any hydroxyl substituents could replace or supplement the waxes used in known ink formulations.

In embodiments, it is desired that the amide (NH) group of the compound be close to the end group of the compound because such a location of the amide (NH) group improves the polarity of the compound. Thus, where $R^1$ includes greater than about 5 carbon atoms, the configuration "close to" in this regard refers to, for example, the amide (NH) group being within about 5 carbons or less of the end of the compound. $R^1$—CONH—$R^2$ may be more desired in terms of polarity to the configuration $R^2$—CONH—$R^1$. Thus, when the compound is utilized in an ink vehicle, polar colorants are better solubulized when the ink vehicle has polar groups, such as the amine group of the disclosed compound.

Examples of alkyl amides having a formula of $R^1$—CONH—$R^2$ or $R^2$—CONH—$R^1$ disclosed herein include:

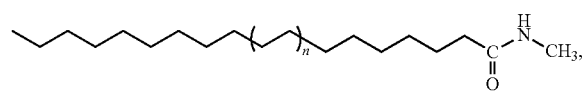

wherein n is, for example, from 0 to about 195, including 0 ($R^1$ derived from stearic acid), 2 ($R^1$ derived from UNICID 350 or behenic acid), 5 ($R^1$ derived from UNICID 425), 10 ($R^1$ derived from UNICID 550) or 15 ($R^1$ derived from UNICID 700);

from about 3 carbon atoms to about 200 carbon atoms, such as from about 5 carbon atoms to about 150 carbon atoms or from about 15 carbon atoms to about 100 carbon atoms. In embodiments, the alkyl group of $R^1$ or $R^3$ may have hydroxyl substitutions and optional heteroatoms, where suitable. For example, if $R^1$ or $R^3$ is a straight chain alkyl, then that alkyl will have no substitutions and no heteroatoms. However if $R^1$ or $R^3$ is a branched alkyl having a hydroxyl substituent, then that $R^1$ or $R^3$ may have substitutions such as heteroatoms, in addition to any hydroxyl substituents. Although $R^1$ and $R^3$ may be the same type of alkyl, in specific embodiments $R^1$ and $R^3$ are not the same type of alkyl, for example, one of $R^1$ and $R^3$ may be a branched alkyl while the other of $R^1$ or $R^3$ may be a straight chain alkyl, or one of $R^1$ and $R^3$ may be an alkyl having a hydroxyl substituent while the other of $R^1$ or $R^3$ may be a straight chain alkyl, or one of $R^1$ and $R^3$ may be a branched alkyl while the other of $R^1$ or $R^3$ may be an alkyl having a hydroxyl substituent.

$R^6$ may be a structure of diaminocyclohexane having a formula of:

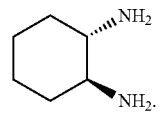

For example, the cyclic di-amides disclosed herein may have a structure of

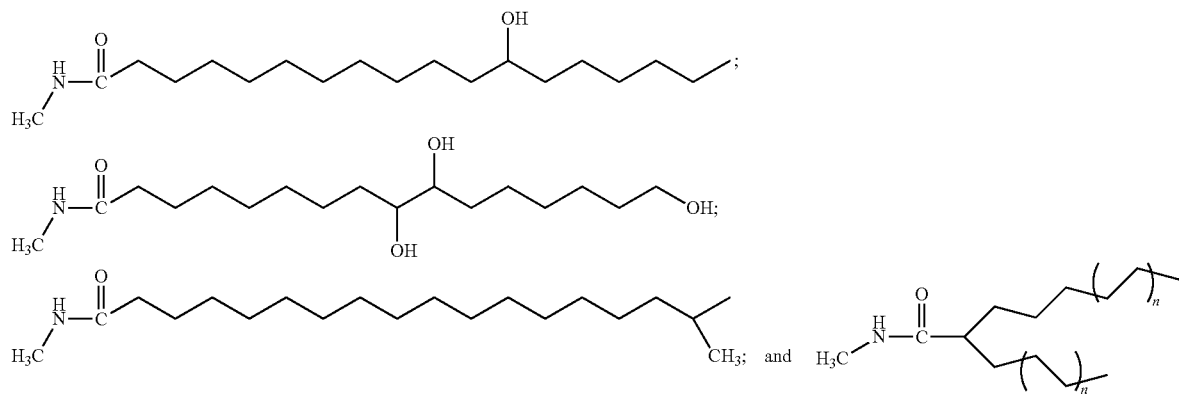

wherein n is, for example, from 0 to 195, and including 0 ($R^1$ 2-ethyl hexanoic acid), 1 ($R^1$ derived from 12 carbon Guerbet acid), 2 ($R^1$ derived from 16 carbon Guerbet acid), 3 ($R^1$ derived from 20 carbon Guerbet acid), 4 ($R^1$ derived from 24 carbon Guerbet acid) or 7 ($R^1$ derived from 36 carbon Guerbet acid).

Di-Amides

In further embodiments, disclosed herein is a di-amide compound having a formula of $R^1$—CONH—$R^6$—CONH—$R^3$, $R^1$—NHCO—$R^6$—CONH—$R^3$, $R^1$—CONH—$R^6$—NHCO—$R^3$ or $R^1$—NHCO—$R^6$—NHCO—$R^3$, wherein the compound is suitable for use in phase change ink compositions, and wherein $R^6$ is cyclic group having from about 5 to about 8 carbon atoms and $R^1$ and $R^3$ are the same or different and comprise straight chain or branched alkyl group having from about 3 carbon atoms to about 200 carbon atoms.

In embodiments, $R^1$ and $R^3$ may be the same or different and comprise a straight chain or branched alkyl group having

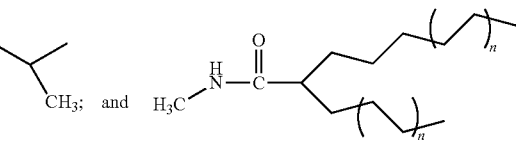

However, $R^6$ is not limited to cyclohexanes, but may also be a cyclopentane, cycloheptane or cyclooctane, and the amines can be present in 1,2 positions, 1,3 positions or 1,4 positions, and may be in the cis position or trans position. $R^6$ can also be an aromatic, an aryl alkyl, an alkyl aryl, and may be substituted or include heteroatoms, as described herein.

The compound having a formula of $R^1$—CONH—$R^6$—CONH—$R^3$, $R^1$—NHCO—$R^6$—CONH—$R^3$, $R^1$—CONH—$R^6$—NHCO—$R^3$ or $R^1$—NHCO—$R^6$—NHCO—$R^3$, may be derived by reacting a sufficient amount of an alkyl amine with a sufficient amount of a straight chain dicarboxylic acid to ensure that the di-amide compound of this embodiment is obtained. This reaction occurs at a temperature in a range of from about 80° C. to about 220° C., such as from about 85° C. to about 215° C. or from about 90° C. to about 210° C. In embodiments, the compound having a formula of $R^1$—NHCO—$R^6$—CONH—$R^3$ may be derived by reacting $R^1$—$CO_2H$, $R^3$—$CO_2H$ and $H_2N$—$R^6$—$H_2N$.

The di-amide compound having a formula of $R^1$—CONH—$R^6$—CONH—$R^3$, $R^1$—NHCO—$R^6$—CONH—$R^3$, $R^1$—CONH—$R^6$—NHCO—$R^3$ or $R^1$—NHCO—$R^6$—NHCO—$R^3$, may be utilized as an ink vehicle, or may replace or supplement known ink components, such as rosin esters, triamides and tetra-amides. When at least one of $R^1$ or $R^3$ is a branched alkyl, then such a compound exhibits improved adhesiveness and flexibility, for example because the branching leads to a higher amorphous content. Such di-amide compounds having at least one of $R^1$ or $R^3$ being a branched alkyl exhibit a low heat of fusion, for example, from about 5 J/g to about 60 J/g, or from about 8 J/g to about 55 J/g or from about 10 J/g to about 50 J/g.

Di-amides compounds derived from straight chain acids are hard at room temperature with a hardness as measured with a Koehler K95500 Digital Penetrometer according to ASTM D1321 being from about 0.01 dmm to about 5 dmm, such as from about 0.1 dmm to about 3.5 dmm or from about 0.5 dmm to about 2 dmm. The viscosities of such di-amide compounds at about 140° C. may be from about 5 cps to about 50 cps, such as from about 8 cps to about 40 cps or from about 10 to about 30 cps. Due to their molecular conformation and their ability to form hydrogen bonds, these materials have relatively high melting and crystallization temperatures of greater than 90° C., such as greater than 100° C. or greater than 110° C.

Di-amide compounds derived from branched carboxylic acids, such as isostearic acid, have viscosities of from about 1 cps to about 500 cps, such as from about 5 cps to about 250 cps or from about 10 cps to about 100 cps at about 140° C. The non-linear molecular conformation of both the trans-1,2-diaminocyclohexane as well as the branched carboxylic acid leads to the formation of materials with low degrees of crystallinity and low heat of fusion of, for example, from about 5 J/g to about 60 J/g, or from about 8 J/g to about 55 J/g or from about 10 J/g to about 50 J/g. While the crystalline portion of such a di-amide compounds may contribute to a low viscosity, the amorphous chains may inhibit the growth of the crystalline domains. As a consequence, these types of materials may display a high degree of flexibility and transparency. They are also thermally stable and display an excellent adhesion to substrates due to the high degree of hydrogen bonding and their permanent flexibility.

Di-amide compounds derived from hydroxyl containing acids may be transparent solids at room temperature, about 25° C. They have lower melting and crystallization transitions than those di-amide compounds derived from straight chain acids with a heat of fusion of from about 5 J/g to about 60 J/g, or from about 8 J/g to about 55 J/g or from about 10 J/g to about 50 J/g.

It is further desired that the amine group of the compound be close to the end group of the compound because such a location of the amine group improves the polarity of the compound. In other words, the term "close" refers to the amine group of the compound being within about 5 carbons or less of the end of the compound. Thus, when the compound is utilized in an ink vehicle, polar colorants are better solubilized when the ink vehicle has polar groups, such as the amine group of the disclosed compound.

Examples of di-amides having a formula of $R^1$—CONH—$R^6$—NHCO—R disclosed herein include:

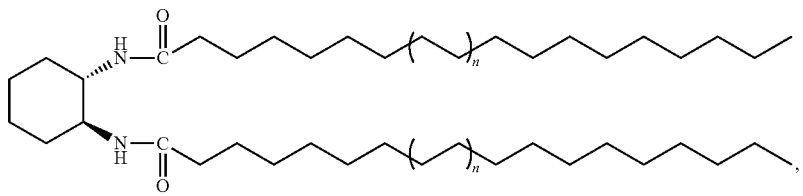

wherein n is, for example, from 0 to about 195, including 0 ($R^1$ derived from stearic acid), 2 ($R^1$ derived from UNICID 350 or behenic acid), 5 ($R^1$ derived from UNICID 425), 10 ($R^1$ derived from UNICID 550) or 15 ($R^1$ derived from UNICID 700); and

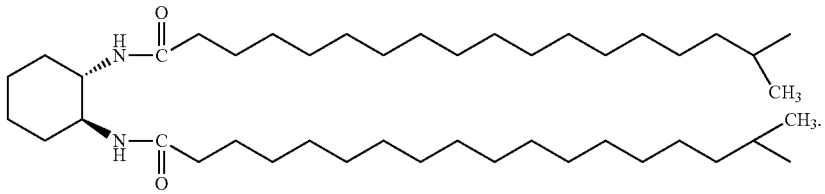

In further embodiments, disclosed herein is a tetra-amide compound having a formula of $R^1$—CONH—$R^6$—CONH—$C_{34}H_{64+n}$—CONH—$R^6$—CONH—$R^3$, $R^1$—NHCO—$R^6$—NHCO—$C_{34}H_{64+n}$—NHCO—$R^6$—NHCO—$R^3$, $R^1$—CONH—$R^6$—NHCO—$C_{34}H_{64+n}$—CONH—$R^6$—NHCO—$R^3$ or $R^1$—NHCO—$R^6$—CONH—$C_{34}H_{64+n}$—NHCO—$R^6$—CONH—$R^3$, wherein $R^6$ is the same or different cyclic group having from about 5 to about 8 carbon atoms and $R^1$ and $R^3$ are the same or different and comprise straight chain or branched alkyl group having from about 3 carbon atoms to about 200 carbon atoms.

$R^6$ may have a structure as defined above for the di-amide disclosed herein. $R^6$ may also be a cyclopentane, cyclohexane, cycloheptane or cyclooctane, and the amine groups may be present at the 1,2 positions, 1,3 positions, 1,4 positions, or 1,5 positions (depending upon the cyclic structure) and may be in the cis position or trans position. $R^6$ can also be an aromatic, an aryl alkyl, an alkyl aryl, and may be substituted or include heteroatoms, as described herein. For example, $R^6$ may be 1,2-trans-diaminocyclohexane having a formula of:

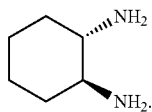

In embodiments, $R^1$ and $R^3$ may be the same or different and comprise a straight chain or branch chained alkyl group having from about 3 carbon atoms to about 200 carbon atoms, such as from about 5 carbon atoms to about 150 carbon atoms or from about 15 carbon atoms to about 10 carbon atoms. In embodiments, the alkyl group of $R^1$ or $R^3$ may have hydroxyl substituents and substitutions such as optional heteroatoms, where suitable. For example, if $R^1$ or $R^3$ is a straight chain alkyl, then that alkyl will have no substituents or substitutions, such as heteroatoms. However, if or $R^1$ or $R^3$ is a branched alkyl having a hydroxyl substituent, then that $R^1$ or $R^3$ may have substituents, in addition to any hydroxyl substituents, and optionally may include substitutions, such as heteroatoms. $R^1$ and $R^3$ do not have to be the same type of alkyl, for example, one of $R^1$ and $R^3$ may be a branched alkyl while the other of $R^1$ or $R^3$ may be a straight chain alkyl, or one of $R^1$ and $R^3$ may be an alkyl having a hydroxyl substituent while the other of $R^1$ or $R^3$ may be a straight chain alkyl, or one of $R^1$ and $R^3$ may be a branched alkyl while the other of $R^1$ or $R^3$ may be an alkyl having a hydroxyl substituent.

A dimer acid suitable for use herein may have a formula of $CO_2H-C_{34}H_{64+n}-CO_2H$, the dimer acid may be a branched alkylene group which may include unsaturations and cyclic groups, wherein n is an integer of 0, 1, 2, 3, 4, 5, 6, 7, 8, 9, or 10.

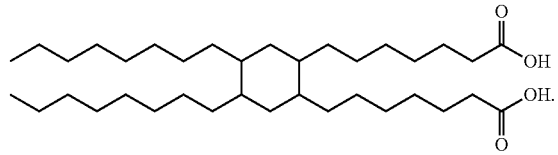

The tetra-amides disclosed herein may have a formula of:

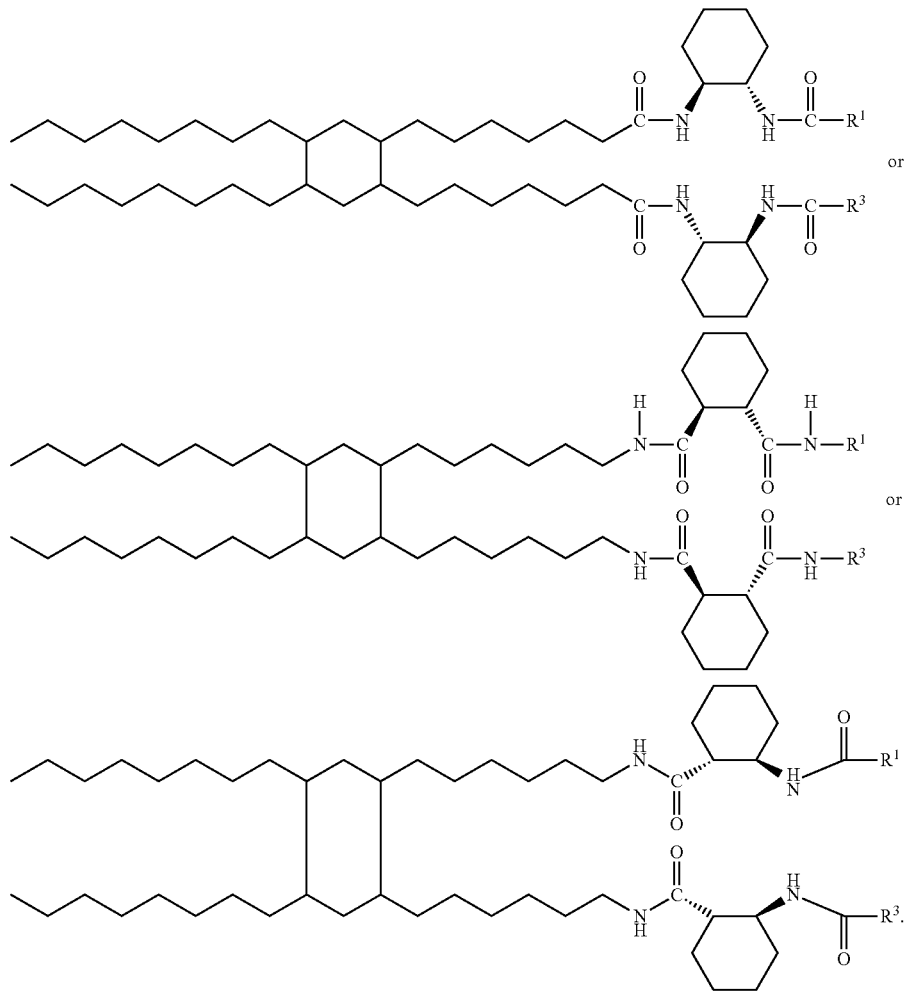

For example, the tetra-amide compound described herein may have the general formula of

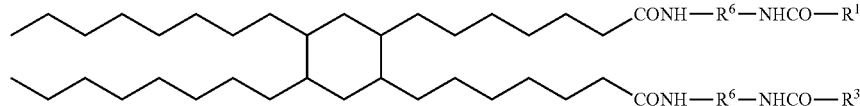

The tetra-amide compound having the above formula may be derived by reacting sufficient amounts of a dimer acid, a cyclic di-amine and carboxylic acid to ensure that the tetra-amide compound of this embodiment is derived. This reaction occurs at a temperature in a range of from about 80° C. to about 220° C., such as from about 85° C. to about 215° C. or from about 90° C. to about 210° C. In embodiments, the tetra-amide compound may be derived by reacting,

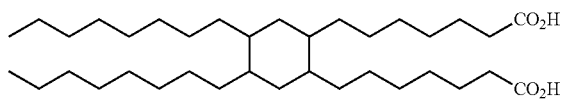

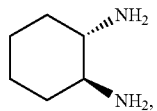

$R^1$—$CO_2H$, and
$R^3$—$CO_2H$, wherein $R^1$ and $R^3$ are defined as above.

The tetra-amide compound having a formula of $R^1$—CONH—$R^6$—CONH—$C_{34}H_{64+n}$—CONH—$R^6$—CONH—$R^3$, $R^1$—CONH—$R^6$—NHCO—$C_{34}H_{64+n}$—CONH—$R^6$—NHCO—$R^3$, $R^1$—NHCO—$R^6$—CONH—$C_{34}H_{64+n}$—NHCO—$R^6$—CONH—$R^3$, $R^1$—NHCO—$R^6$—NHCO—$C_{34}H_{64+n}$—CONH—$R^6$—CONH—$R^3$, and $R^1$—CONH—$R^6$—CONH—$C_{34}H_{64+n}$—NHCO—$R^6$—NHCO—$R^3$, may be utilized as a phase change ink vehicle. When at least one of $R^1$ or $R^3$ is a branched alkyl, such a compound exhibits unexpected results over existing triamide components and existing tetra-amide components used in known ink formulations, such as improved adhesiveness and flexibility, for example because the branching leads to a higher amorphous content. The tetra-amide described herein may be utilized in known ink formulations as a replacement for or a supplement to known rosin esters, known triamides and known tetra-amides.

Tetra-amide compounds derived from straight chain acids are very hard at room temperature, about 25° C., with a hardness measured with a Koehler K95500 Digital Penetrometer according to ASTM D1321 being from about 0.01 dmm (decimillimeters) to about 5 dmm, such as from about 0.1 dmm to about 3 dmm or from about 0.5 dmm to about 1 dmm. Their viscosities at about 140° C. may be from about 25 cps to about 600 cps, such as from about 40 cps to about 400 cps or from about 50 cps to about 200 cps, depending upon the chain length of the acid used. The longer straight chain acids lead to materials with higher degrees of crystallinity, lower melt viscosities and are more opaque, with heat of fusion that can range from about 25 J/g to about 600 J/g, or from about 50 J/g to about 400 J/g or from about 100 J/g to about 200 J/g. The tetra-amide compounds with shorter straight chain acids are more amorphous, have higher viscosities and at the same time exhibit improved transparency and heat of fusion that can range from about 5 J/g to about 60 J/g, or from about 8 J/g to about 55 J/g or from about 10 J/g to about 50 J/g.

In tetra-amide compounds derived from branched carboxylic acid, the use of 1,2-trans-diaminocyclohexane in the synthesis of tetra-amides leads to materials that have a higher amorphous component and as a result, they are hard and transparent. The use of branched carboxylic acids contributes even more to a disruption of the chain linearity and leads to materials that range from semicrystalline to amorphous. Such tetra-amide compounds derived from branched carboxylic acids have a lower melting point transitions as well as improved toughness. They may have viscosities of from about 25 cps to about 1000 cps, such as from about 50 cps to about 750 cps or from about 100 cps to about 500 cps at a temperature of about 140° C. The non-linear molecular conformation of both the trans-1,2-diaminocyclohexane as well as the branched carboxylic acid leads to the formation of materials with low degrees of crystallinity and low heat of fusion that can range from about 5 J/g to about 60 J/g, or from about 8 J/g to about 55 J/g or from about 10 J/g to about 50 J/g.

Tetra-amide compounds derived from hydroxyl containing carboxylic acids have similar properties to tetra-amide compounds derived from branched carboxylic acids except that viscosities can range from about 25 cps to about 5000 cps, such as from about 50 cps to about 2500 cps or from about 100 cps to about 1000 cps at a temperature of 140° C., and a heat of fusion that can range from about 5 J/g to about 60 J/g, or from about 8 J/g to about 55 J/g or from about 10 J/g to about 50 J/g.

Examples of tetra-amide compounds having a formula of $R^1$—CONH—$R^6$—CONH—$C_{34}H_{64+n}$—CONH—$R^6$—CONH—$R^3$, $R^1$—CONH—$R^6$—NHCO—$C_{34}H_{64+n}$—CONH—$R^6$—NHCO—$R^3$ or $R^1$—NHCO—$R^6$—CONH—$C_{34}H_{64+n}$—NHCO—$R^6$—CONH—$R^3$, $R^1$—NHCO—$R^6$—NHCO—$C_{34}H_{64+n}$—CONH—$R^6$—CONH—$R^3$, and $R^1$—CONH—$R^6$—CONH—$C_{34}H_{64+n}$—NHCO—$R^6$—NHCO—$R^3$, disclosed herein include:

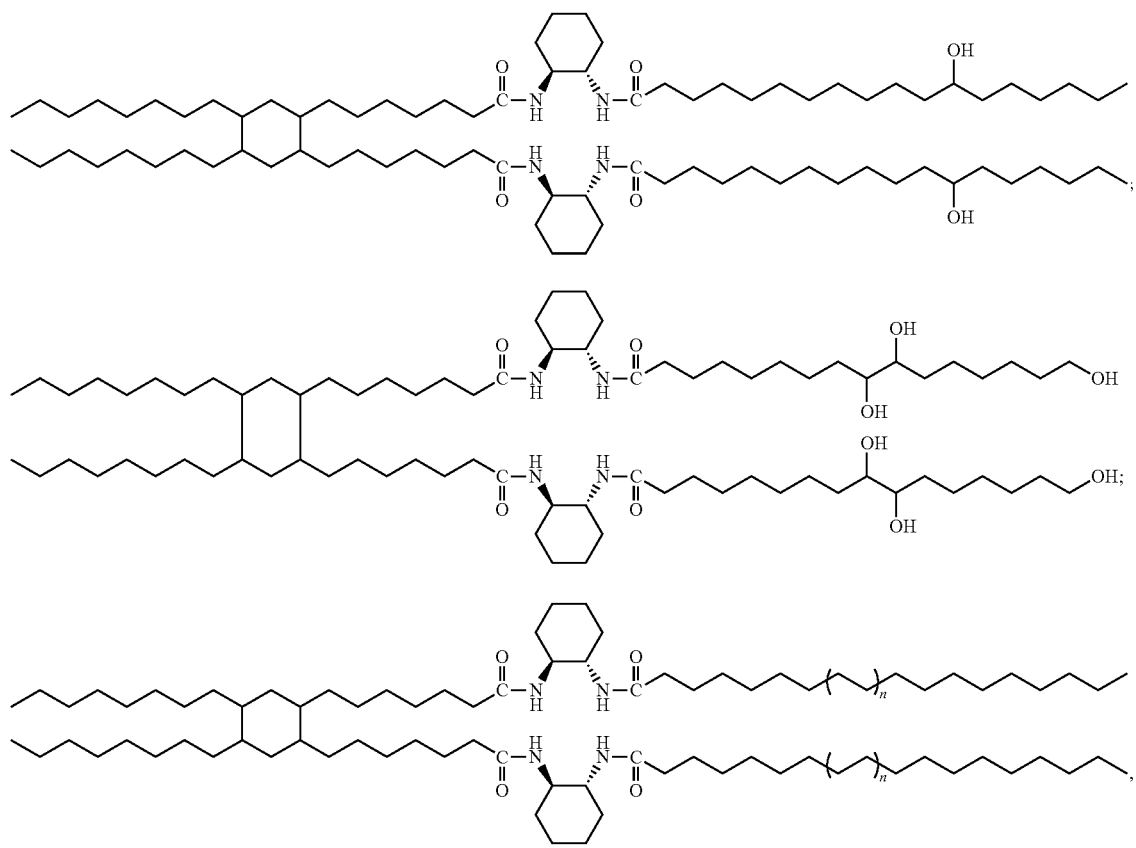
wherein n is, for example, from 0 to about 195, including 0 (R¹ derived from stearic acid), 2 (R¹ derived from UNICID 350 or behenic acid), 5 (R¹ derived from UNICID 425), 10 (R¹ derived from UNICID 550) or 15 (R¹ derived from UNICID 700);
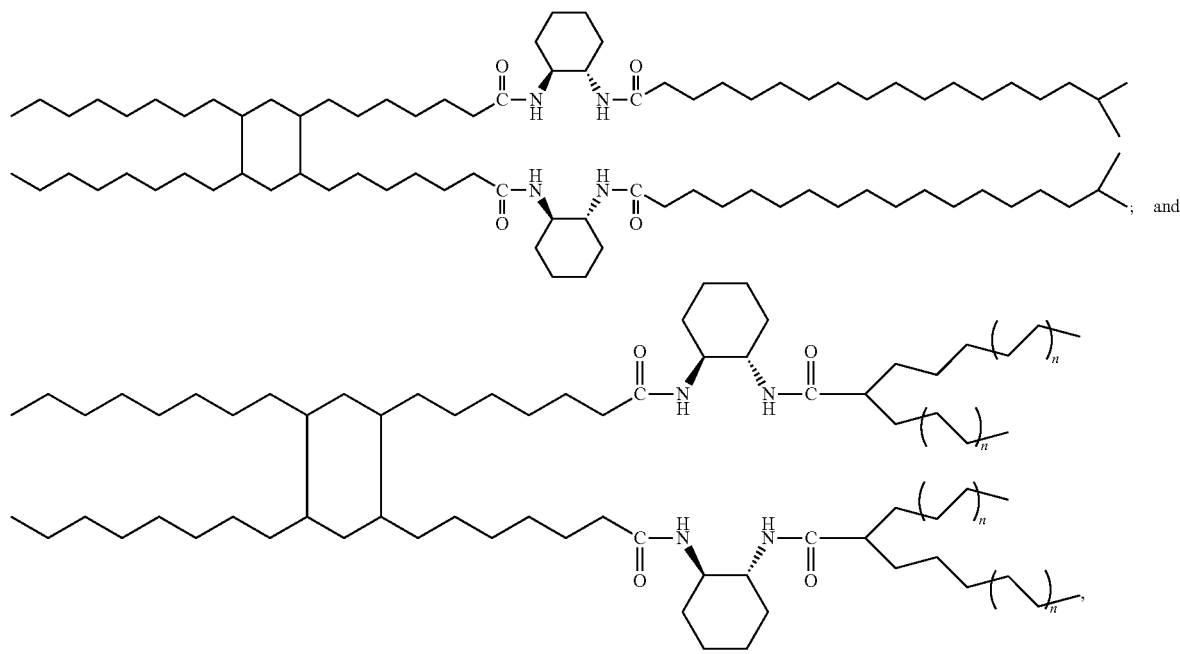

wherein n is, for example, from 0 to about 195, and including 0 (derived from 2-ethyl hexanoic acid), 1 (derived from 12 carbon Guerbet acid), 2 (derived from 16 carbon Guerbet acid), 3 (20 carbon Guerbet acid), 4 (derived from 24 carbon Guerbet acid) or 7 (derived from 36 carbon Guerbet acid).

In yet further embodiments, disclosed is a tetra-amide compound having a formula of $R^1$—CONH—$R^4$—CONH—$C_{34}H_{64+n}$—CONH—$R^5$—CONH—$R^3$, $R^1$—CONH—$R^4$—NHCO—$C_{34}H_{64+n}$—CONH—$R^5$—NHCO—$R^3$ or $R^1$—NHCO—$R^4$—CONH—$C_{34}H_{64+n}$—NHCO—$R^5$—CONH—$R^3$, $R^1$—NHCO—$R^4$—NHCO—$C_{34}H_{64+n}$—CONH—$R^5$—CONH—$R^3$, or $R^1$—CONH—$R^4$—CONH—$C_{34}H_{64+n}$—NHCO—$R^5$—NHCO—$R^3$, wherein $R^1$ and $R^3$ are the same as described above for other tetra-amide compounds. $R^1$ and $R^3$ may both be derived from isostearic acid.

$R^6$ in the tetra-amides described above are replaced with $R^4$ or $R^5$, which may be the same or different alkylene having from 1 to about 200 carbon atoms, such as from about 3 to about 150 carbon atoms or from about 5 to about 100 carbon atoms.

For example, a tetra-amide compound having a formula of $R^1$—CONH—$R^4$—CONH—$C_{34}H_{64+n}$—CONH—$R^5$—CONH—$R^3$, $R^1$—CONH—$R^4$—NHCO—$C_{34}H_{64+n}$—CONH—$R^5$—NHCO—$R^3$ or $R^1$—NHCO—$R^4$—CONH—$C_{34}H_{64+n}$—NHCO—$R^5$—CONH—$R^3$, $R^1$—NHCO—$R^4$—NHCO—$C_{34}H_{64+n}$—CONH—$R^5$—CONH—$R^3$, or $R^1$—CONH—$R^4$—CONH—$C_{34}H_{64+n}$—NHCO—$R^5$—NHCO—$R^3$ may be

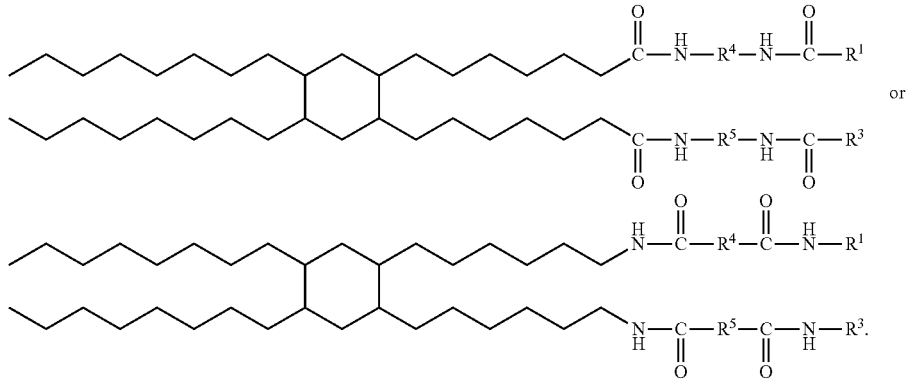

Each of the amide compounds described herein may be present in a phase change ink as an ink vehicle in any suitable amount. Specifically, any of the amide compounds may be present alone or in combination in an amount of from about 5 weight percent to about 100 weight percent of the ink vehicle of the phase change ink, such as from about 10 weight percent to about 95 weight percent of the ink vehicle of the phase change ink or from about 15 weight percent to about 90 weight percent of the ink vehicle of the phase change ink.

Additional Ink Components

Any additional suitable ink vehicle components may be employed, although as above it may be desirable for the amide compound to comprise substantially all of the ink vehicle. Additional suitable ink vehicle materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers such as further discussed below, and mixtures thereof.

Examples of suitable additional specific ink vehicle materials include, for example, ethylene/propylene copolymers, such as those available from Petrolite and of the general formula

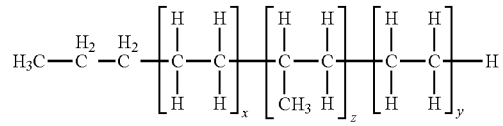

wherein z represents an integer from 0 to about 30, such as from 0 to about 20 or from 0 to about 10, y represents an integer from 0 to about 21, such as from 0 to about 20 or from 0 to about 10 and x is equal to about 21-y. The distribution of the side branches may be random along the carbon chain. The copolymers may have, for example, a melting point of from about 70° C. to about 150° C., such as from about 80° C. to about 130° C. or from about 90° C. to about 120° C. and a molecular weight range of from about 500 to about 4,000. Commercial examples of such copolymers include, for example, Petrolite CP-7 (Mn=650), Petrolite CP-11 (Mn=1,100, Petrolite CP-12 (Mn=1,200) and the like. When present, the ethylene/propylene copolymers may be present in an amount of from about 1 percent to about 80 percent by weight of the ink vehicle, in another embodiment from about 3 percent to about 70 by weight of the ink vehicle, in yet another embodiment at least about 5 percent to about 60 percent by weight of the ink vehicle.

Urethane, urea, amide and imide derivatives of oxidized synthetic or petroleum waxes, such as those available from Petrolite and of the general formulas

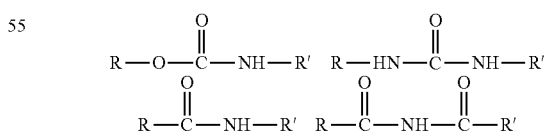

wherein R is an alkyl group of the formula $CH_3(CH_2)_n$, n is an integer of from about 5 to about 400, for example from about 10 to about 300 or from about 20 to about 200 and R' is a tolyl group, may also be used as the ink vehicle. In embodiments, the urethane, urea, amide and imide derivatives may be linear, branched, cyclic and any combination thereof. These materials may have a melting point of from about 60° C. to about 120° C., such as from about 70° C. to about 100° C. or from about 70° C. to about 90° C. Commercial examples of such materials include, for example, PETROLITE CA-11 (Mn=790, Mw/Mn=2.2), PETROLITE WB-5 (Mn=650, Mw/Mn=1.7), PETROLITE WB-17 (Mn=730, Mw/Mn=1.8), and the like.

When present, urethane resin may be present in the ink in one embodiment in an amount of from about 1 percent to about 80 percent by weight of the ink vehicle, in another embodiment from about 3 percent to about 70 by weight of the ink vehicle, in yet another embodiment at least about 5 percent to about 60 percent by weight of the ink vehicle. Similarly, when present, urea, amide and imide derivatives of oxidized synthetic or petroleum waxes may be present in an amount of from about 1 percent to about 80 percent by weight of the ink vehicle, in another embodiment from about 3 percent to about 70 by weight of the ink vehicle, in yet another embodiment at least about 5 percent to about 60 percent by weight of the ink vehicle.

Another type of ink vehicle may be n-paraffinic, branched paraffinic, and/or aromatic hydrocarbons, typically with from about 5 to about 100, such as from about 20 to about 180 or from about 30 to about 60 carbon atoms, generally prepared by the refinement of naturally occurring hydrocarbons, such as BE SQUARE 185 and BE SQUARE 195, with molecular weights (Mn) of from about 100 to about 5,000, such as from about 250 to about 1,000 or from about 500 to about 800, for example such as available from Petrolite.

Highly branched hydrocarbons, typically prepared by olefin polymerization, such as the VYBAR materials available from Petrolite, including VYBAR 253 (Mn=520), VYBAR 5013 (Mn=420), and the like, may also be used. In addition, the ink vehicle may be an ethoxylated alcohol, such as available from Petrolite and of the general formula

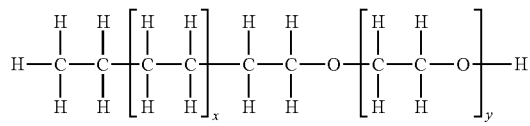

wherein x is an integer of from about 1 to about 50, such as from about 5 to about 40 or from about 11 to about 24 and y is an integer of from about 1 to about 70, such as from about 1 to about 50 or from about 1 to about 40. The materials may have a melting point of from about 60° C. to about 150° C., such as from about 70° C. to about 120° C. or from about 80° C. to about 110° C. and a molecular weight (Mn) range of from about 100 to about 5,000, such as from about 500 to about 3,000 or from about 500 to about 2,500. Commercial examples include UNITHOX 420 (Mn=560), UNITHOX 450 (Mn=900), UNITHOX 480 (Mn=2,250), UNITHOX 520 (Mn=700), UNITHOX 550 (Mn=1,100), UNITHOX 720 (Mn=875), UNITHOX 750 (Mn=1,400), and the like. When present, highly branched hydrocarbons may be present in an amount of from about 1 percent to about 80 percent by weight of the ink vehicle, in another embodiment from about 3 percent to about 70 by weight of the ink vehicle, in yet another embodiment at least about 5 percent to about 60 percent by weight of the ink vehicle.

As an additional example of highly branched hydrocarbons, mention may be made of fatty amides, such as monoamides, tetra-amides, mixtures thereof, and the like. Suitable monoamides may have a melting point of at least about 50° C., for example from about 50° C. to about 150° C., although the melting point can be below this temperature. Specific examples of suitable monoamides include, for example, primary monoamides and secondary monoamides. Stearamide, such as KEMAMIDE S available from Witco Chemical Company and CRODAMIDE S available from Croda, behenamide/arachidamide, such as KEMAMIDE B available from Witco and CRODAMIDE BR available from Croda, oleamide, such as KEMAMIDE U available from Witco and CRODAMIDE OR available from Croda, technical grade oleamide, such as KEMAMIDE O available from Witco, CRODAMIDE O available from Croda, and UNISLIP 1753 available from Uniqema, and erucamide such as KEMAMIDE E available from Witco and CRODAMIDE ER available from Croda, are some examples of suitable primary amides. Behenyl behenamide, such as KEMAMIDE EX666 available from Witco, stearyl stearamide, such as KEMAMIDE S-180 and KEMAMIDE EX-672 available from Witco, stearyl erucamide, such as KEMAMIDE E-180 available from Witco and CRODAMIDE 212 available from Croda, erucyl erucamide, such as KEMAMIDE E-221 available from Witco, oleyl palmitamide, such as KEMAMIDE P-181 available from Witco and CRODAMIDE 203 available from Croda, and erucyl stearamide, such as KEMAMIDE S-221 available from Witco, are some examples of suitable secondary amides. Additional suitable amide materials include KEMAMIDE W40 (N,N'-ethylenebisstearamide), KEMAMIDE P181 (oleyl palmitamide), KEMAMIDE W45 (N,N'-thylenebisstearamide), and KEMAMIDE W20 (N,N'-ethylenebisoleamide).

High molecular weight linear alcohols, such as those available from Petrolite and of the general formula

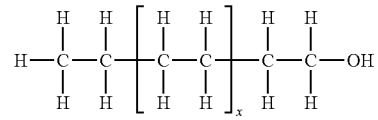

wherein x is an integer of from about 1 to about 50, such as from about 5 to about 35 or from about 11 to about 23, may also be used as the ink vehicle. These materials may have a melting point of from about 50° C. to about 150° C., such as from about 70° C. to about 120° C. or from about 75° C. to about 110° C., and a molecular weight (Mn) range of from about 100 to about 5,000, such as from about 200 to about 2,500 or from about 300 to about 1,500. Commercial examples include the UNILIN materials such as UNILIN 425 (Mn~460), UNILIN 550 (Mn~550), UNILIN 700 (Mn~700), and the like.

A still further example includes hydrocarbon-based waxes, such as the homopolymers of polyethylene available from Petrolite and of the general formula

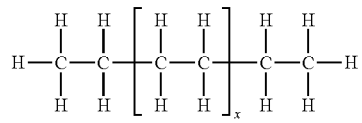

wherein x is an integer of from about 1 to about 200, such as from about 5 to about 150 or from about 12 to about 105. These materials may have a melting point of from about 60° C. to about 150° C., such as from about 70° C. to about 140° C. or from about 80° C. to about 130° C. and a molecular weight (Mn) of from about 100 to about 5,000, such as from about 200 to about 4,000 or from about 400 to about 3,000.

Example waxes include the line of waxes, such as POLYWAX 500 (Mn=500), POLYWAX 655 (Mn=655), POLYWAX 850 (Mn=850), POLYWAX 1000 (Mn=1,000), and the like.

Another example includes modified maleic anhydride hydrocarbon adducts of polyolefins prepared by graft copolymerization, such as those available from Petrolite and of the general formulas

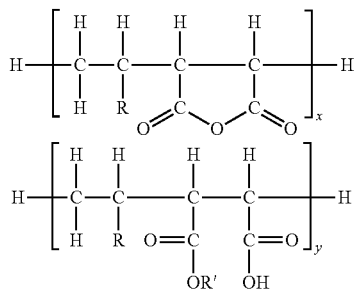

wherein R is an alkyl group with from about 1 to about 50, such as from about 5 to about 35 or from about 6 to about 28 carbon atoms, R' is an ethyl group, a propyl group, an isopropyl group, a butyl group, an isobutyl group, or an alkyl group with from about 5 to about 500, such as from about 10 to about 300 or from about 20 to about 200 carbon atoms, x is an integer of from about 9 to about 13, and y is an integer of from about 1 to about 50, such as from about 5 to about 25 or from about 9 to about 13, and having melting points of from about 50° C. to about 150° C., such as from about 60° C. to about 120° C. or from about 70° C. to about 100° C.; those available from Petrolite and of the general formula

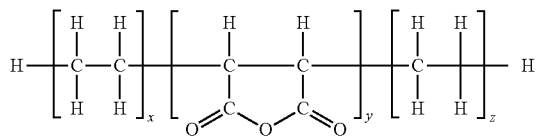

wherein x is an integer of from about 1 to about 50, such as from about 5 to about 25 or from about 9 to about 13, y is 1 or 2, and z is an integer of from about 1 to about 50, such as from about 5 to about 25 or from about 9 to about 13; and those available from Petrolite and of the general formula

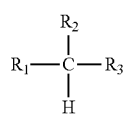

wherein $R_1$ and $R_3$ are hydrocarbon groups and $R_2$ is either of one of the general formulas

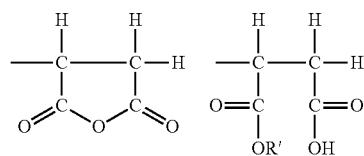

or a mixture thereof, wherein R' is an isopropyl group, which materials may have melting points of from about 70° C. to about 150° C., such as from about 80° C. to about 130° C. or from about 90° C. to about 125° C., with examples of modified maleic anhydride copolymers including CERAMER 67 (Mn=655, Mw/Mn=1.1), CERAMER 1608 (Mn=700, Mw/Mn=1.7), and the like.

Additional examples of suitable additional ink vehicle materials for the phase change inks include rosin esters, such as glyceryl abietate (KE-100®); polyamides; dimer acid amides; fatty acid amides, including ARAMID C; epoxy resins, such as EPOTUF 37001, available from Riechold Chemical Company; fluid paraffin waxes; fluid microcrystalline waxes; Fischer-Tropsch waxes; polyvinyl alcohol resins; polyols; cellulose esters; cellulose ethers; polyvinyl pyridine resins; fatty acids; fatty acid esters; poly sulfonamides, including KETJENFLEX MH and KETJENFLEX MS80; benzoate esters, such as BENZOFLEX S552, available from Velsicol Chemical Company; phthalate plasticizers; citrate plasticizers; maleate plasticizers; polyvinyl pyrrolidinone copolymers; polyvinyl pyrrolidone/polyvinyl acetate copolymers; novolac resins, such as DUREZ 12 686, available from Occidental Chemical Company; and natural product waxes, such as beeswax, montan wax, candelilla wax, GILSONITE (American Gilsonite Company), and the like; mixtures of linear primary alcohols with linear long chain amides or fatty acid amides, such as those with from about 6 to about 24 carbon atoms, including PARICIN 9 (propylene glycol monohydroxystearate), PARICIN 13 (glycerol monohydroxystearate), PARICIN 15 (ethylene glycol monohydroxystearate), PARICIN 220 (N(2-hydroxyethyl)-12-hydroxystearamide), PARICIN 285 (N,N'-ethylene-bis-12-hydroxystearamide), FLEXRICIN 185 (N,N'-ethylene-bis-ricinoleamide), and the like. Further, linear long chain sulfones with from about 4 to about 16 carbon atoms, such as diphenyl sulfone, n-amyl sulfone, n-propyl sulfone, n-pentyl sulfone, n-hexyl sulfone, n-heptyl sulfone, n-octyl sulfone, n-nonyl sulfone, n-decyl sulfone, n-undecyl sulfone, n-dodecyl sulfone, n-tridecyl sulfone, n-tetradecyl sulfone, n-pentadecyl sulfone, n-hexadecyl sulfone, chlorophenyl methyl sulfone, and the like, are suitable ink vehicle materials. These additional examples of suitable ink vehicles may be present in the ink vehicle in any suitable amount for example from about 1 to about 90 weight percent of the ink vehicle, such as from about 5 to about 60 weight percent or from about 10 to about 30 weight percent of the ink vehicle.

The ink vehicle may comprise one or more of the aforementioned suitable materials. As used herein, "one or more" and "at least one" refers to from 1 to about 10, such as from 1 to about 8 or from 1 to about 5 of any given feature disclosed herein.

The ink vehicle may comprise from about 25% to about 99.5% by weight of the ink, for example from about 30% to about 90% or from about 50% to about 85% by weight of the ink.

The phase change inks also contain at least one colorant, for example, from 1 to about 10, such as from 1 to about 4 or from 1 to about 2 colorants. The colorant is present in the ink in any desired amount, typically from about 0.5 to about 75 percent by weight of the ink vehicle, for example from about 1 to about 50 percent by weight of the ink vehicle.

Examples of suitable colorants include pigments, dyes, mixtures of pigments and dyes, mixtures of pigments, mixtures of dyes, and the like. Any dye or pigment may be chosen, provided that it is capable of being dispersed or dissolved in the ink vehicle and is compatible with the other ink components.

Examples of suitable pigments include, for example, Violet PALIOGEN Violet 5100 (BASF); PALIOGEN Violet 5890 (BASF); HELIOGEN Green L8730 (BASF); LITHOL Scarlet D3700 (BASF); SUNFAST® Blue 15:4 (Sun Chemical 249-0592); Hostaperm Blue B2G-D (Clariant); Permanent Red P-F7RK; Hostaperm Violet BL (Clariant); LITHOL Scarlet 4440 (BASF); Bon Red C (Dominion Color Company); ORACET Pink RF (Ciba); PALIOGEN Red 3871 K (BASF); SUNFAST® Blue 15:3 (Sun Chemical 249-1284); PALIOGEN Red 3340 (BASF); SUNFAST® Carbazole Violet 23 (Sun Chemical 246-1670); LITHOL Fast Scarlet L4300 (BASF); Sunbrite Yellow 17 (Sun Chemical 275-0023); HELIOGEN Blue L6900, L7020 (BASF); Sunbrite Yellow 74 (Sun Chemical 272-0558); SPECTRA PAC® C Orange 16 (Sun Chemical 276-3016); HELIOGEN Blue K6902, K6910 (BASF); SUNFAST® Magenta 122 (Sun Chemical 228-0013); HELIOGEN Blue D6840, D7080 (BASF); Sudan Blue OS (BASF); NEOPEN Blue FF4012 (BASF); PV Fast Blue B2GO1 (Clariant); IRGALITE Blue BCA (Ciba); PALIOGEN Blue 6470 (BASF); Sudan Orange G (Aldrich), Sudan Orange 220 (BASF); PALIOGEN Orange 3040 (BASF); PALIOGEN Yellow 152, 1560 (BASF); LITHOL Fast Yellow 0991 K (BASF); PALIOTOL Yellow 1840 (BASF); NOVOPERM Yellow FGL (Clariant); Lumogen Yellow D0790 (BASF); Suco-Yellow L1250 (BASF); Suco-Yellow D1355 (BASF); Suco Fast Yellow D1355, D1351 (BASF); HOSTAPERM Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA Magenta (DU PONT), PALIOGEN Black L0084 (BASF); Pigment Black K801 (BASF); and carbon blacks such as REGAL 330™ (Cabot), Carbon Black 5250, Carbon Black 5750 (Columbia Chemical), mixtures thereof and the like.

Examples of suitable dyes include, for example, Usharect Blue 86 (Direct Blue 86), available from Ushanti Color; Intralite Turquoise 8GL (Direct Blue 86), available from Classic Dyestuffs; Chemictive Brilliant Red 7BH (Reactive Red 4), available from Chemiequip; Levafix Black EB, available from Bayer; Reactron Red $H_8B$ (Reactive Red 31), available from Atlas Dye-Chem; D&C Red #28 (Acid Red 92), available from Warner-Jenkinson; Direct Brilliant Pink B, available from Global Colors; Acid Tartrazine, available from Metrochem Industries.; Cartasol Yellow 6GF Clariant; Carta Blue 2GL, available from Clariant; and the like.

In embodiments, solvent dyes may be utilized. Examples of solvent dyes include spirit soluble dyes which are compatible with the ink vehicles disclosed herein. Examples of suitable spirit solvent dyes include Neozapon Red 492 (BASF); Orasol Red G (Ciba); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow CGP (Ciba); Orasol Black RLP (Ciba); Savinyl Black RLS (Clariant); Morfast Black Conc. A (Rohm and Haas); Orasol Blue GN (Ciba); Savinyl Blue GLS (Sandoz); Luxol Fast Blue MBSN (Pylam); Sevron Blue 5GMF (Classic Dyestuffs); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 260501] (BASF) and the like. Other suitable colorants include non-polar dyes, such as those disclosed in U.S. Pat. Nos. 6,472,523, 6,713,614, 6,958,406, 6,998,493, 7,211,131 and 7,294,730, each of which is incorporated herein by reference in its entirety.

Examples of suitable propellants for the phase change inks include, for example, water; hydrazine; alcohols such as ethanol, propanol, butanol, 2,5-dimethyl-2,5-hexanediol, 3-hydroxy benzyl alcohol, and the like; cyclic amines and ureas, including 1,3-dimethyl urea such as imidazole, substituted imidazoles, including 2-imidazolidone, 2-ethyl imidazole, 1,2,4-triazole, and the like; pyrazole and substituted pyrazoles, including 3,5-dimethylpyrazole and the like; pyrazine; carboxylic acids; sulfonic acids; aldehydes and ketones; hydrocarbons such as biphenyl, hexane, benzene; esters; phenols, including phenol, dichlorophenol, other halogen substituted phenols, and cresols; amides such as propionamide, lactamide, and the like; imides; halocarbons; urethanes; ethers; sulfones, including dimethyl sulfone, methyl sulfone, diethyl sulfone, and diphenyl sulfone; sulfamides such as methyl sulfamide; sulfonamides such as ortho, para-toluenesulfonamide, methyl sulfonamide, and the like; phosphites; phosphonates; phosphates; alkyl sulfides such as methyl sulfide; alkyl acetates such as methyl acetate; sulfur dioxide; alkylene carbonates such as propylene carbonate; succinimide; and the like. Sulfones such as dimethyl sulfone, diethyl sulfone, diphenyl sulfone, and the like, and any mixtures thereof, may also be used.

The ink of embodiments may further include conventional additives to take advantage of the known functionality associated with such conventional additives. Such additives may include, for example, biocides, defoamers, slip and leveling agents, plasticizers, pigment dispersants, viscosity modifiers, antioxidants, absorbers, etc.

Optional biocides may be present in amounts of from about 0.1 to about 1.0 percent by weight of the ink. Suitable biocides include, for example, sorbic acid, 1-(3-chloroallyl)-3,5,7-triaza-1-azoniaadamantane chloride, commercially available as DOWICIL 200 (Dow Chemical Company), vinylene-bis thiocyanate, commercially available as CYTOX 3711 (American Cyanamid Company), disodium ethylenebis-dithiocarbamate, commercially available as DITHONE D14 (Rohm & Haas Company), bis(trichloromethyl)sulfone, commercially available as BIOCIDE N-1386 (Stauffer Chemical Company), zinc pyridinethione, commercially available as zinc omadine (Olin Corporation), 2-bromo-t-nitropropane-1,3-diol, commercially available as ONYXIDE 500 (Onyx Chemical Company), BOSQUAT MB50 (Louza, Inc.), and the like. In addition, other optional additives such as dispersing agents or surfactants may be present in the inks, typically in amounts of from about 0.01 to about 20 percent by weight. Plasticizers that may be used include pentaerythritol tetrabenzoate, commercially available as BENZOFLEX 5552 (Velsicol Chemical Corporation), trimethyl titrate, commercially available as CITROFLEX 1 (Monflex Chemical Company), N,N-dimethyl oleamide, commercially available as HALCOMID M-18-OL (C. P. Hall Company), a benzyl phthalate, commercially available as SANTICIZER 278 (Ferro Corporation), and the like, may be added to the ink vehicle, and may constitute from about 1 to 100 percent of the ink vehicle component of the ink. Plasticizers can either function as the ink vehicle or can act as an agent to provide compatibility between the ink propellant, which generally is polar, and the ink vehicle, which generally is non-polar.

The viscosity modifier may be (1) 2-hydroxybenzyl alcohol, (2) 4-hydroxybenzyl alcohol, (3) 4-nitrobenzyl alcohol, (4) 4-hydroxy-3-methoxy benzyl alcohol, (5) 3-methoxy-4-nitrobenzyl alcohol, (6) 2-amino-5-chlorobenzyl alcohol, (7) 2-amino-5-methylbenzyl alcohol, (8) 3-amino-2-methylbenzyl alcohol, (9) 3-amino-4-methyl benzyl alcohol, (10) 2(2-(aminomethyl)phenylthio) benzyl alcohol, (11) 2,4,6-trimethylbenzyl alcohol, (12) 2-amino-2-methyl-1,3-propanediol, (13) 2-amino-1-phenyl-1,3-propanediol, (14) 2,2-dimethyl-1-phenyl-1,3-propanediol, (15) 2-bromo-2-nitro-1,3-propanediol, (16) 3-tert-butylamino-1,2-propanediol, (17) 1,1-diphenyl-1,2-propanediol, (18) 1,4-dibromo-2,3-butanediol, (19) 2,3-dibromo-1,4-butanediol, (20) 2,3-dibromo-2-butene-1,4-diol, (21) 1,1,2-triphenyl-1,2-ethanediol, (22) 2-naphthalenemethanol, (23) 2-methoxy-1-naphthalenemethanol, (24) decafluoro benzhydrol, (25) 2-methylbenzhydrol, (26) 1-benzeneethanol, (27) 4,4'-isopropylidene bis(2-(2,6-dibromo phenoxy)ethanol), (28) 2,2'-(1,4-phenylenedioxy)diethanol, (29) 2,2-bis(hydroxymethyl)-2,2',2''-nitrilotriethanol, (30) di(trimethylolpropane), (31) 2-amino-3-phenyl-1-propanol, (32) tricyclohexylmethanol, (33) tris(hydroxymethyl)aminomethane succinate, (34) 4,4'-trimethylene bis(1-piperidine ethanol), (35) N-methyl glucamine, (36) xylitol, or mixtures thereof. When present, the viscosity modifier is present in the ink in any effective amount, such as from about 30 percent to about 55 percent by weight of the ink or from about 35 percent to about 50 percent by weight of the ink.

The optional antioxidants of the ink compositions protect the images from oxidation and also protect the ink components from oxidation during the heating portion of the ink preparation process. Specific examples of suitable antioxidants include NAUGUARD® 524, NAUGUARD® 76, and NAUGUARD® 512 (commercially available from Uniroyal Chemical Company, Oxford, Conn.), IRGANOX® 1010 (commercially available from Ciba Geigy), and the like. The antioxidant, when present, may be present in the ink in any desired or effective amount, such as from about 0.25 percent to about 10 percent by weight of the ink or from about 1 percent to about 5 percent by weight of the ink.

The ink can also optionally contain a UV absorber. The optional UV absorbers primarily protect the generated images from UV degradation. Specific examples of suitable UV absorbers include (1) 2-bromo-2',4-dimethoxyacetophenone (Aldrich 19,948-6), (2) 2-bromo-2',5'-dimethoxyacetophenone (Aldrich 10,458-2), (3) 2-bromo-3'-nitroacetophenone (Aldrich 34,421-4), (4) 2-bromo-4'-nitroacetophenone (Aldrich 24,561-5), (5) 3',5'-diacetoxyacetophenone (Aldrich 11,738-2), (6) 2-phenylsulfonyl acetophenone (Aldrich 34,150-3), (7) 3'-aminoacetophenone (Aldrich 13,935-1), (8) 4'-aminoacetophenone (Aldrich A3,800-2), (9) 1H-benzotriazole-1-acetonitrile (Aldrich 46,752-9), (10) 2-(2H-benzotriazol-2-yl)-4,6-di-tert-pentylphenol (Aldrich 42,274-6), (11) 1,1-(1,2-ethane-diyl)bis(3,3,5,5-tetramethylpiperazinone) (commercially available from Goodrich Chemicals), (12) 2,2,4-trimethyl-1,2-hydroquinoline (commercially available from Mobay Chemical), (13) 2-(4-benzoyl-3-hydroxy phenoxy)ethylacrylate, (14) 2-dodecyl-N-(1,2,2,6,6-pentamethyl-4-piperidinyl) succinimide (commercially available from Aldrich Chemical Co., Milwaukee, Wis.), (15) 2,2,6,6-tetramethyl-4-piperidinyl/β-tetramethyl-3,9-(2,4,8,10-tetraoxo spiro(5,5)-undecane) diethyl-1,2,3,4-butane tetracarboxylate (commercially available from Fairmount), (16) N-(p-ethoxycarbonylphenyl)-N'-ethyl-N'-phenylformadine (commercially available from Givaudan), (17) 6-ethoxy-1,2-dihydro-2,2,4-trimethylquinoline (commercially available from Monsanto Chemicals), (18) 2,4,6-tris-(N-1,4-dimethylpentyl-4-phenylenediamino)-1,3,5-triazine (commercially available from Uniroyal), (19) 2-dodecyl-N-(2,2,6,6-tetrame-thyl-4-piperidinyl) succinimide (commercially available from Aldrich Chemical Co.), (20) N-(1-acetyl-2,2,6,6-tetramethyl-4-piperidinyl)-2-dodecyl succinimide (commercially available from Aldrich Chemical Co.), (21) (1,2,2,6,6-pentamethyl-4-piperidinyl/β-tetramethyl-3,9-(2,4,8,10-tetra oxo-spiro-(5,5)undecane)diethyl)-1,2,3,4-butane tetracarboxylate (commercially available from Fairmount), (22) (2,2,6,6-tetramethyl-4-piperidinyl)-1,2,3,4-butane tetracarboxylate (commercially available from Fairmount), (23) nickel dibutyl dithio carbamate (commercially available as UV-Chek AM-105 from Ferro), (24) 2-amino-2',5-dichlorobenzophenone (Aldrich 10,515-5), (25) 2'-amino-4',5'-dimethoxyacetophenone (Aldrich 32,922-3), (26) 2-benzyl-2-(dimethylamino)-4'-morpholino butyrophenone (Aldrich 40,564-7), (27) 4'-benzyloxy-2'-hydroxy-3'-methylacetophenone (Aldrich 29,884-0), (28) 4,4'-bis(diethylamino) benzophenone (Aldrich 16,032-6), (29) 5-chloro-2-hydroxy benzophenone (Aldrich C4,470-2), (30) 4'-piperazinoacetophenone (Aldrich 13,646-8), (31) 4'-piperidinoacetophenone (Aldrich 11,972-5), (32) 2-amino-5-chlorobenzophenone (Aldrich A4,556-4), (33) 3,6-bis(2-methyl-2-morpholinopropionyl)-9-octylcarbazole (Aldrich 46,073-7), and the like, such as the UV absorbers described in U.S. Pat. No. 7,084,189, which is incorporated herein in its entirety by reference, as well as mixtures thereof. When present, the optional UV absorber may be present in the ink in any desired or effective amount, such as from about 1 percent to about 10 percent by weight of the ink or from about 3 percent to about 5 percent by weight of the ink.

The ink compositions can be prepared by any desired or suitable method. For example, the ink ingredients can be mixed together, followed by heating, to a temperature in one embodiment of at least about 100° C., and in one embodiment of no more than about 140° C., although the temperature can be outside of these ranges, and stirring until a homogeneous ink composition is obtained, followed by cooling the ink to ambient temperature (typically from about 20 to about 25° C.). The inks are solid at ambient temperature. In a specific embodiment, during the formation process, the inks in their molten state are poured into molds and then allowed to cool and solidify to form ink sticks of any desired shape.

Printed images may be generated with the ink described herein by incorporating the ink into an ink jet device, for example a thermal ink jet device, an acoustic ink jet device or a piezoelectric ink jet device, and concurrently causing droplets of the molten ink to be ejected in a pattern onto a substrate such as paper or transparency material, which can be recognized as an image. The ink is typically included in the at least one reservoir connected by any suitable feeding device to the ejecting channels and orifices of the ink jet head for ejecting the ink. In the jetting procedure, the ink jet head may be heated, by any suitable method, to the jetting temperature of the inks. The phase change inks are thus transformed from the solid state to a molten state for jetting. "At least one" or "one or more" as used to describe components of the ink jet device, such as the ejecting channels, orifices, etc., refers to from 1 to about 2 million, such as from about 1000 to about 1.5 million or about 10,000 to about 1 million of any such component found in the ink jet device. "At least one" or "one or more" as used to describe other components of the ink jet device such as the ink jet head, reservoir, feeder, etc., refers to from 1 to about 15, such as from 1 to about 8 or from 1 to about 4 of any such component found in the ink jet device.

The inks can also be employed in indirect (offset) printing ink jet applications, wherein when droplets of the melted ink are ejected in an imagewise pattern onto a recording substrate, the recording substrate is an intermediate transfer member and the ink in the imagewise pattern is subsequently transferred from the intermediate transfer member to a final recording substrate, such as paper or transparency.

Embodiments described above will now be further illustrated by way of the following examples.

EXAMPLES OF METHYL AMIDES

Derived from Hydroxyl Containing Carboxylic Acids

Example 1

About 500 g of 12-hydroxystearic acid (available from Caschem) was added to a 4 necked 1 L kettle having a heating mantle, nitrogen flow, distillation arm, mechanical Tru-Bore Stirrer, and thermocouple running to a temperature controller unit from Watlow. The temperature was set at about 120° C. and allowed to heat. After about 50 minutes, the temperature had reached about 133° C. and all of the contents were molten. The stirrer was turned on. The temperature was set at about 110° C., and the mantle was lowered to facilitate cooling. When the temperature had reached about 106° C., the mantle was raised and the addition of about 161.4 g of about 33% methylamine in ethyl alcohol (available from Aldrich) was initiated through a 250 mL addition funnel. Addition was completed in about 3 minutes, the temperature had dropped to about 95° C., and the initial distilled solvent collected by the distillation arm was returned to kettle. The temperature was set at about 180° C., and the mixture was allowed to heat while being stirred for about 5 hours. The mixture was poured into an aluminum foil pan and allowed to cool. The viscosity of the tan waxy solid was about 20.2 cps as measured by a Ferranti-Shirley cone-plate viscometer at about 135° C.

The methyl amide of Example 1 has the following formula:

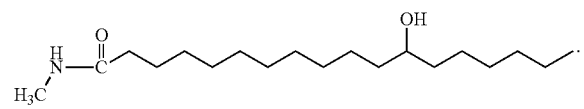

Example 2

About 31.7 g of aleuritic acid (available from Sabinsa Corp) was added to a 100 mL 1-necked 45/50 round bottom tube having a condenser, $N_2$ blowing through top of condenser and Teflon coated magnet. The reaction flask was placed in about a 130° C. oil bath and stirring was initiated. After about 30 minutes, about 16.5 grams of about 33% methylamine solution in ethanol (available from Aldrich Chemical Company) was added. The temperature of the oil bath was increased to about 150° C., and stirred at this temperature for about 1.5 hours. The condenser was then replaced with a distillation setup and a $N_2$ stream was introduced where the thermometer would be placed in the distillation head. The $N_2$ was distilled off the water while the reaction mixture was stirred at about 150° C. for about an additional 2 hours. The oil bath temperature controller was then increased to about 190° C., and the reaction mixture was stirred with $N_2$ distillation for about 1 hour after reaching this temperature. The nitrogen inlet tube was then removed, and a vacuum was introduced to distill all unreacted volatiles out of the flask for about 1 hour. The mixture was poured into aluminum pans and allowed to cool. The viscosity of the solid product was about 163.8 cps as measured by a Ferranti-Shirley cone-plate viscometer at about 135° C.

The methyl amide of Example 2 has the following formula:

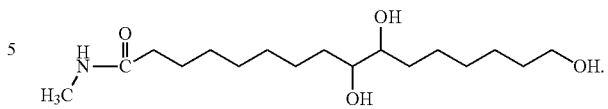

Characterization of Methyl Amides Derived from Hydroxyl Containing Carboxylic Acids The rheological measurements were performed on the RFS3 Fluids Rheometer in the dynamic mode, using the 50 mm cone and a gap of 53 microns. The test performed was a temperature step sweep from about 140° C. to about 50° C. at a constant frequency of about 1 Hz. The methyl-amides derived from the hydroxyl containing carboxylic acids do not display any crystallinity due to their low molecular weight and the non-linearity of the 12-hydroxystearic and aleuritic acids, respectively. They have a low viscosity in the melt, they are solids at about room temperature, approximately 25° C., due to the hydrogen bonding and at the same time the hydroxyl functionality leads to increased hydrophilicity. Due to these properties, these methyl amides may be utilized as replacements for KE100 resins in various ink formulations.

Derived from Straight Chained Carboxylic Acids

Example 3

About 500 g of stearic acid (available from Aldrich) was added to a 4 necked 1 L kettle with heating mantle, nitrogen flow, distillation arm, mechanical Tru-Bore Stirrer, and a thermocouple running to a temperature controller unit from Watlow. The temperature was set at about 120° C. and allowed to heat. After about 25 minutes, the temperature had reached about 120° C. and all solids were molten. The stirrer was turned on. The temperature was set at about 110° C. and the mantle was lowered to facilitate cooling. When the temperature had reached about 115° C., the mantle was raised and the addition of about 169.7 g of about 33% methylamine in ethyl alcohol (available from Aldrich) was initiated through a 250 mL addition funnel. Addition was completed in about 3 minutes, the temperature had dropped to about 95° C., and the initial distilled solvent collected by the distillation arm was returned to the kettle. Slight yellowing of the mixture was observed after addition of the methylamine. The temperature was set at about 180° C., and the mixture was allowed to heat under stirring for about 5 hours. The mixture was poured into an aluminum foil pan and allowed to cool. The viscosity of the tan waxy solid was about 1.02 cps as measured by a Ferranti-Shirley cone-plate viscometer at about 135° C.

The methyl amide of Example 3 has the following formula:

where n is 1.

Example 4

About 500 g of UNICID 425 (available from Baker Petrolite) was added to a 4 necked 1 L kettle with heating mantle, nitrogen flow, distillation arm, mechanical Tru-Bore Stirrer, and thermocouple running to a temperature controller unit from Watlow was charged. The temperature was set at about 120° C. and allowed to heat. After about 40 minutes the temperature had reached about 114° C. and all solids were molten. The stirrer was turned on. Temperature was set at about 110° C. When the temperature had reached about 114° C., the addition of about 84 g of about 33% methylamine in ethyl alcohol (available from Aldrich) was initiated through a 250 mL addition funnel. Addition was complete in about 3 minutes, the temperature had dropped to about 95° C., and the initial distilled solvent collected by the distillation arm was returned to kettle. The temperature was set at about 180° C. and the mixture was allowed to heat under stirring for about 5 hours. The mixture was poured into an aluminum foil pan and allowed to cool. The viscosity of the tan waxy solid was about 11.97 cps as measured by a Ferranti-Shirley cone-plate viscometer at about 135° C.

The methyl amide of Example 4 has the following formula:

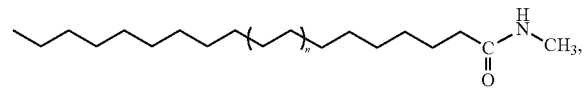

where n is 6.

Example 5

About 500 g UNICID 550 (available from Baker Petrolite) was added to a 4 necked 1 L kettle having a heating mantle, nitrogen flow, distillation arm, mechanical Tru-Bore Stirrer, and thermocouple running to a temperature controller unit from Watlow. The temperature was set at about 120° C. and allowed to heat. After about 65 minutes, the temperature had reached about 127° C. and all solids were molten. The stirrer was turned on. The temperature was set at about 110° C. When temperature had reached about 112° C., the addition of about 65.5 g of about 33% methylamine in ethyl alcohol (available from Aldrich) was initiated through a 250 mL addition funnel. Addition was complete in about 3 minutes, white solids observed at methylamine point of contact, and the initial distilled solvent collected by the distillation arm was returned to kettle. The temperature was set at about 180° C. and the mixture was allowed to heat under stirring for about 5 hours. Mixture was poured into an aluminum foil pan and allowed to cool. The viscosity of the tan waxy solid was about 9 cps as measured by a Ferranti-Shirley cone-plate viscometer at about 135° C.

The methyl amide of Example 5 has the following formula:

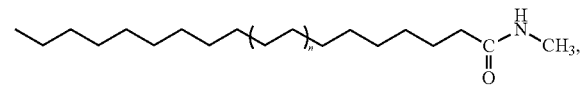

where n is 11.

Example 6

About 750 g UNICID 700 (available from Baker Petrolite) was added to a 4 necked 1 L kettle having a heating mantle, nitrogen flow, distillation arm, mechanical Tru-Bore Stirrer, and thermocouple running to a temperature controller unit from Watlow. The temperature was set at about 120° C. and allowed to heat. After about 65 minutes, the temperature had reached about 128° C. and all solids were molten. The stirrer was turned on, and the temperature went to about 118° C. and the addition of about 65.2 g of about 33% methylamine in ethyl alcohol (available from Aldrich) was initiated through a 250 mL addition funnel. Addition was complete in about 3 minutes, and white solids were observed at methylamine point of contact. The temperature was set at about 180° C. and the mixture was allowed to heat under stirring for about 5 hours. The mixture was poured into an aluminum foil pan and allowed to cool. The viscosity of the tan waxy solid was about 11.67 cps as measured by a Ferranti-Shirley cone-plate viscometer at about 135° C.

The methyl amide of Example 6 has the following formula:

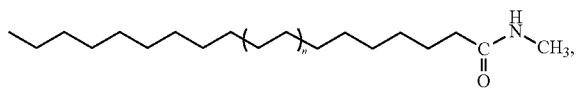

where n is 16.

Example 7

About 500 g UNICID 350 (available from Baker Petrolite) was added to a 4 necked 1 L kettle having a heating mantle, nitrogen flow, distillation arm, mechanical Tru-Bore Stirrer, and thermocouple running to a temperature controller unit from Watlow. The temperature was set at about 120° C. and allowed to heat. After about 25 minutes, the temperature had reached about 104° C. and all solids were molten. The stirrer was turned on. The temperature was set at about 100° C. When the temperature had reached about 104° C. the addition of about 65.5 g of about 33% methylamine in ethyl alcohol (available from Aldrich) was initiated through a 250 mL addition funnel. Addition was complete in about 3 minutes, and the temperature had dropped to about 95° C. The temperature was set at about 180° C., and the mixture was allowed to heat while being stirring for about 5 hours. The mixture was poured into an aluminum foil pan and allowed to cool. The viscosity of the tan waxy solid was about 2.89 cps as measured by a Ferranti-Shirley cone-plate viscometer at about 135° C.

The methyl amide of Example 7 has the following formula:

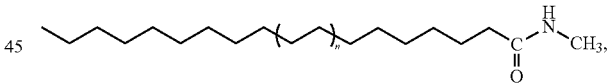

where n is 3.

Example 8

About 500 g PRIFRAC 2989 behenic acid (available from Uniqema) was added to a 4 necked 1 L kettle having a heating mantle, nitrogen flow, distillation arm, mechanical Tru-Bore Stirrer, and thermocouple running to a temperature controller unit from Watlow. The temperature was set at about 120° C. and allowed to heat. After about 15 minutes, the temperature had reached about 104° C. and all solids were molten. The stirrer was turned on. The temperature was set at about 100° C. When the temperature had reached about 111° C., the addition of about 135.8 g of about 33% methylamine in ethyl alcohol (available from Aldrich) was initiated through a 250 mL addition funnel. Addition was completed in about 3 minutes, and the temperature had dropped to about 96° C. Slight yellowing of mixture was observed following addition of the methylamine. The temperature was set at about 180° C. and the mixture was allowed to heat under stirring for about 4 hours. The mixture was poured into an aluminum foil pan and allowed to cool.

The methyl amide of Example 8 has the following formula:

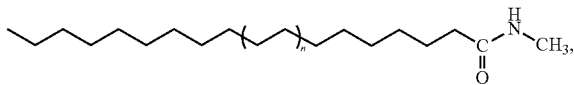

where n is 3.

Characterization of Methyl Amides Derived from Straight Chained Carboxylic Acids The rheological measurements were performed on an RFS3 Fluids Rheometer available from TA Instruments in the dynamic mode, using the 50 mm cone and a gap of 53 microns. The test performed was a temperature step sweep from about 140° C. to about 90° C. at a constant frequency of about 1 Hz. From about 140° C. to a temperature slightly above the onset of crystallization temperature, about 5° C. decrements were used with an equilibration time of about 180 seconds at each temperature, followed by about 2° C. steps to about 90° C. at about 120 seconds intervals to determine the crystallization transition more accurately. Upon heating, about a 140° C. was achieved in about 5° C. steps to determine the temperature when there is a complete re-melting of the crystalline structure.

The viscosity at about 110° C. as well as at the onset of crystallization temperatures are a function of the chain length of the starting acid used in the reaction. This enables the control of the viscosity and the onset of crystallization temperature of the final ink. The methyl-amide based on the shorter chain stearic acid (Example 3) could have a dual role; it could be a replacement for POLYWAX resins currently used in ink formulations because they have a similar viscosity but at the same time, the methyl-amide is a dye solubilizer and has superior miscibility with the other ink components. The other methyl-amides derived from longer straight chained carboxylic acids could be used as viscosity improvers and ink compatibilizers in various ink formulations.

Data for Examples 1-8 is demonstrated below in Table 1.

Derived from Branched Carboxylic Acids

Example 9

About 500 g of isostearic acid (available as PRISORINE 3505 from Uniqema) was added to a 1000 mL 3-necked round bottom flask with condenser in the middle neck, a glass stopper in each of the other 2 outside necks, N₂ blowing through top of condenser, and with a Teflon coated magnet. The reaction flask was placed in about a 110° C. oil bath and stirring was initiated. After about 5 minutes, about 165 grams of about 33% methyl amine (in about 67% ethanol available from Aldrich Chemical Company) was added slowly over about 15 minutes through the condenser. The reaction mixture was allowed to stir for about 1 hour at about 110° C. The oil bath temperature controller was then increased to about 150° C. and the reaction mixture stirred for about 30 minutes after reaching this temperature. The temperature controller was then increased to about 190° C. After about 2 hours at about 190° C., the condenser was replaced with a glass stopper (in the middle neck), a distillation setup was attached to one of the outside necks, and a N₂ stream attached to the other neck. The N₂ was distilled off the water while the reaction mixture was stirred at about 190° C. for 2 about hours. The product was poured into a glass jar and allowed to cool. The viscosity of the viscous liquid was about 2.9 cps as measured by a Ferranti-Shirley cone-plate viscometer at about 135° C.

The methyl amide of Example 9 has the following formula:

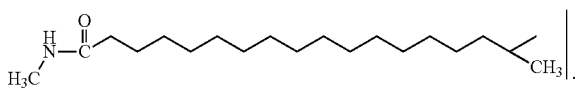

Example 10

About 60 g of ISOCARB 24 acid (available from Condea Vista Corp) was added to about a 100 mL 1-necked 45/50 round bottom tube with condenser and N2 blowing through the top of the condenser, and with a Teflon coated magnet. The

| Example | Type | Acid | Viscosity @ 140° C. (cps) | Viscosity @ 110° C. (cps) | Onset of crystallization (° C.) Rheology | Peak Melting (° C.) - DSC | Heat of fusion (J/g) - DSC | Hardness (dmm at RT) |
|---|---|---|---|---|---|---|---|---|
| 1 | Methylamine | 12-hydroxy-stearic acid | 18.5 | 27.6 | 38.0 | N/A | N/A | — |
| 2 | " | aleuritic acid | 130.1 | 448.2 | 45.0 | N/A | N/A | — |
| 3 | " | C18 - Stearic Acid | 3.2 | 5.7 | 64.0 | 65.5 | 189.0 | 7.5 |
| 8 | " | C22 - Behenic Acid | 4.3 | 6.7 | 75.0 | 77.3 | 211.5 | 3.5 |
| 7 | " | C22 - UNICID 350 | 5.0 | 8.9 | 85.0 | 72.7 | 170.0 | 4.0 |
| 4 | " | C28 - UNICID 425 | 6.1 | 10.3 | 95.0 | 87.9 | 257.5 | 2.0 |
| 5 | " | C38 - UNICID 550 | 8.2 | 15.7 | 99.0 | 101.8 | 236.1 | 1.0 |
| 6 | " | C48 - UNICID 700 | 9.7 | 21.3 | 104.0 | 106.1 | 225.3 | 0.5 | reaction flask was placed in about a 100° C. oil bath and stirring was initiated once all of the solid was melted. After about 60 minutes, about 16 grams of a about 33% methylamine solution in ethanol (available from Aldrich Chemical Company) was added. The temperature of the oil bath was increased to about 150° C. and stirred at this temperature for about 1.5 hours. The condenser was then replaced with a distillation setup, which was distilled off the water while the reaction mixture stirred at about 150° C. for about an additional 2 hours. The oil bath temperature controller was then increased to about 190° C., and the reaction mixture was stirred with distillation for about 1 hour after reaching this temperature. A nitrogen inlet tube was then placed subsurface and gentle $N_2$ bubbling was introduced to distill all unreacted volatiles out of the flask for about 1 hour. The mixture was poured into aluminum pans and allowed to cool. The viscosity of the solid product was about 3.34 cps as measured by a Ferranti-Shirley cone-plate viscometer at about 135° C.

The methyl amide of Example 10 has the following formula:

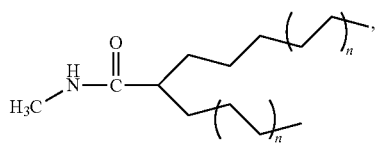

where n is 4.

Example 11

About 40 g of 2-ethylhexanoic acid (available from Aldrich Chemical Corp) was added to about a 100 mL 1-necked 45/50 round bottom tube with a condenser and $N_2$ blowing through top of the condenser, and with Teflon coated magnet. The reaction flask was placed in about a 120° C. oil bath and stirring was initiated. After about 160 minutes, about 27 grams of about 33% methylamine solution in ethanol (available from Aldrich Chemical Company) was added. The temperature of the oil bath was increased to about 150° C. and stirred at this temperature for about 1.5 hours. The condenser was then replaced with a distillation setup, which distilled off the water while the reaction mixture was stirred at about 150° C. for about an additional 2 hours. The oil bath temperature controller was then increased to about 190° C. and the reaction mixture was stirred with distillation for about 1 hour after reaching this temperature. A nitrogen inlet tube was then placed subsurface and gentle $N_2$ bubbling was introduced to distill all unreacted volatiles out of the flask for about 1 hour. The viscous liquid was poured into a jar and allowed to cool.

The methyl amide of Example 11 has the following formula:

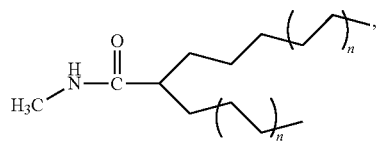

where n is 0.

Characterization of Methyl Amides Derived from Branched Carboxylic Acids

The use of branched carboxylic acids in the synthesis of methyl-amides led to the formation of materials with a low viscosities and low degrees of crystallinity. As with other classes of materials, the chain length of the acid used has a major impact on the properties of the amides such as mechanical properties and viscosity. The ones described in Examples 9 and 11 are liquid at about room temperature, approximately 25° C., with viscosities at about 110° C. of about 5.5 cps and about 1.2 cps, respectively.

The methyl-amide with Isocarb 24 acid described in Example 10 had a higher chain length and was a solid at about room temperature, approximately 25° C. It had a viscosity of about 5.0 cps at about 110° C. and an onset of crystallization temperature of about 55° C.

Examples of Di-Amides Derived from Branched Carboxylic Acids

Example 12

About 100 g of isostearic acid (available as Prisorine 3505 from Uniqema) was added to a 1000 mL 3-necked round bottom flask having a condenser in the middle neck, a glass stopper in each of the other 2 outside necks, $N_2$ blowing through top of condenser and a Teflon coated magnet. The reaction flask was placed in about a 120° C. oil bath and stirring was initiated. After about 5 minutes, about 19.7 g of trans-1,2-diaminocyclohexane (available from Aldrich Chemical Company) was added through one of the side arms. The reaction mixture was stirred for about 10 minutes at about 120° C. The oil bath temperature controller was then increased to about 190° C. and the reaction mixture was stirred for about 1 hour after reaching this temperature. The condenser was then replaced with a glass stopper (in the middle neck), a distillation setup was attached to one of the outside necks and a $N_2$ stream was attached to the other neck. The $N_2$ was distilled off the water while the reaction mixture was stirred at about 190° C. for about an additional 2 hours. The reaction product was then poured into aluminum tins and allowed to solidify.

The di-amide of Example 12 has the following formula:

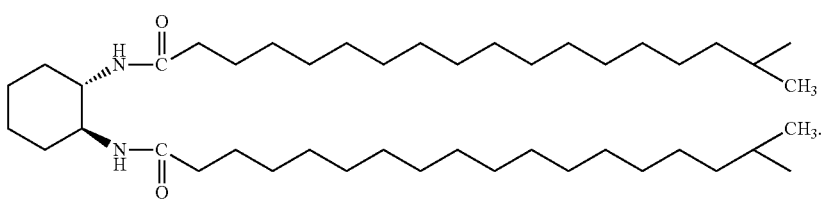

Example 13

About 50 g of isostearic acid (available as Prisorine 3505 from Uniqema) and a Teflon coated magnet were added to a 100 mL 45/50 1-necked round bottom tube. A 45/50 4-neck adaptor was then attached to the 45/50 tube. A condenser was placed in the middle neck, a $N_2$ inlet was placed in one of the necks and a glass stopper was placed in each of the other 2 necks. The reaction flask was placed in about a 120° C. oil bath and stirring was initiated. After about 1 hour, about 10.6 grams of trans-1,2-diaminocyclohexane (available from Aldrich Chemical Company) was added through one of the necks and the stopper was replaced. The reaction mixture was stirred for about 1 hour at a temperature of about 120° C. The oil bath temperature controller was then increased to about 190° C. and the reaction mixture was stirred for about 4 hours after reaching this temperature. The product was then poured into aluminum tins. The viscosity of the solid product was about 20 cps as measured by a Ferranti-Shirley cone-plate viscometer at a temperature of about 135° C.

The di-amide of Example 13 has the following formula:

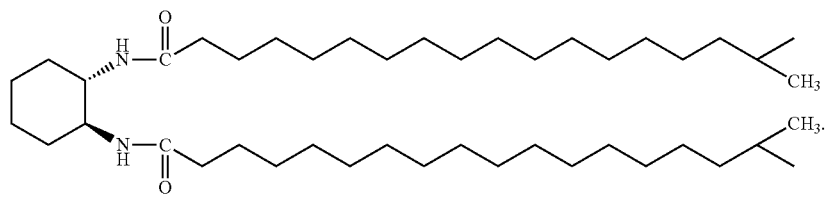

Example 14

About 50 g of C-32 Guerbet Acid (available as Isocarb 32 from Condea Vista) and a Teflon coated magnet were added to a 100 mL 45/50 1-necked round bottom tube. A 45/50 4-neck adaptor was then attached to the 45/50 tube. A condenser was placed in the middle neck, a $N_2$ inlet was placed in one of the necks and a glass stopper was placed in each of the other 2 necks. The reaction flask was placed in about a 120° C. oil bath and stirring was initiated. After about 1 hour, about 5.5 g of trans-1,2-diaminocyclohexane (available from Aldrich Chemical Company) was added through one of the necks and the stopper replaced. The reaction mixture was stirred for about 1 hour at a temperature of about 120° C. The oil bath temperature controller was then increased to a temperature of about 190° C. and the reaction mixture stirred for about 4 hours after reaching this temperature. The product was then poured into aluminum tins.

The di-amide of Example 14 has the following formula:

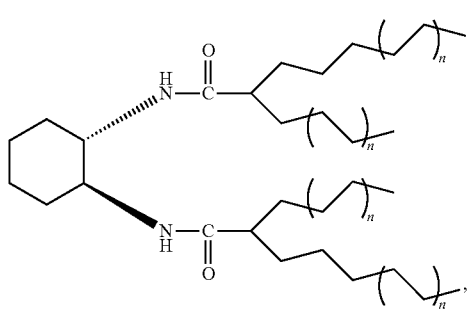

where n is 5.

Example 15

About 50 g of C-24 Guerbet Acid (available as Isocarb 24 from Condea Vista) and a Teflon coated magnet were added to a 100 mL 45/50 1-necked round bottom tube. A 45/50 4-neck adaptor was then attached to the 45/50 tube. A condenser was placed in the middle neck, a $N_2$ inlet was placed in one of the necks and a glass stopper was placed in each of the other 2 necks. The reaction flask was placed in about a 120° C. oil bath and stirring was initiated. After about 1 hour, about 7.7 grams of trans-1,2-diaminocyclohexane (available from Aldrich Chemical Company) was added through one of the necks and the stopper replaced. The reaction mixture was stirred for about 1 hour at a temperature of about 120° C. The oil bath temperature controller was then increased to about 190° C. and the reaction mixture was stirred for about 4 hours after reaching this temperature. The product was then poured into aluminum tins.

The di-amide of Example 15 has the following formula:

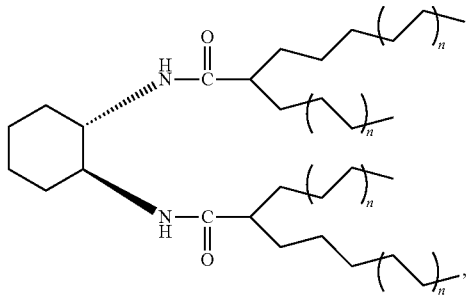

where n is 4.

Example 16

About 806 g of neooctanoic acid (availalbe from Exxon Corp) was added To a 100 mL 1-necked 45/50 round bottom tube having a condenser, $N_2$ blowing through the top of the condenser and a Teflon coated magnet. The reaction flask was placed in about a 130° C. oil bath and stirring was initiated. After about 30 minutes, about 31.3 grams of trans-1,2-diaminocyclohexane (available from Aldrich Chemical Company) was added. The temperature of the oil bath was increased to about 150° C. and stirred at this temperature for about 1.5 hours. The condenser was then replaced with a distillation setup and a $N_2$ stream was introduced where the thermometer would be placed in the distillation head. The $N_2$ distilled off the water while the reaction mixture was stirred at about 150° C. for about an additional 2 hours. The oil bath temperature controller was then increased to about 190° C. and the reaction mixture was stirred with $N_2$ distillation for about 1 hour after reaching this temperature. The nitrogen inlet tube was then removed and a vacuum was introduced to distill all unreacted volatiles out of the flask for about 1 hour. The mixture was poured into aluminum pans and allowed to cool.

The di-amide of Example 16 has the following formula:

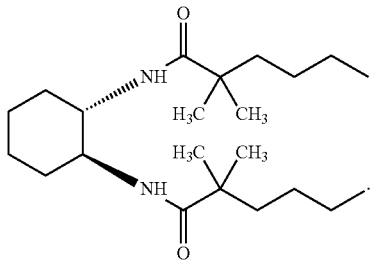

Characterization of Di-amides Derived from Branched Carboxylic Acids

Due to the non-linear molecular conformation of both the trans-1,2-diaminocyclohexane as well as the branched carboxylic acid, these di-amides have unusual properties. While the crystalline fraction contributes to a low viscosity (about 43 cps at a temperature of about 120° C.), the amorphous chains inhibit the growth of the crystalline domains. As a result, these types of di-amide materials display a high degree of flexibility and transparency. They are also thermally stable and display excellent adhesion to substrates due to the high degree of hydrogen bonding and their permanent flexibility. The onset of crystallization temperature can be tailored by the ratio between reaction components, such as the trans-1,2-diaminocyclohexane and the branched carboxylic acid.

Derived from Hydroxyl Containing Carboxylic Acids

Example 17

About 200 g of 12-hydroxystearic acid (available from Caschem) was added to a 1000 mL 3-necked round bottom flask with a condenser in the middle neck, a glass stopper in each of the other 2 outside necks, $N_2$ blowing through top of condenser and Teflon coated magnet. The reaction flask was placed in an about 110° C. oil bath and stirring was initiated. After about 30 minutes, about 38 grams of trans-1,2-diaminocyclohexane (available from Aldrich Chemical Company) was added through one of the side arms. The reaction mixture was allowed to stir for about 10 minutes at about 120° C. The oil bath temperature controller was then increased to about 150° C. and the reaction mixture was stirred for about 1 hour after reaching this temperature. The condenser was then replaced with a glass stopper (in the middle neck), a distillation setup was attached to one of the outside necks and a $N_2$ stream attached to the other neck. The $N_2$ distilled off the water while the reaction mixture stirred at about 150° C. for about an additional 2 hours. The oil bath temperature controller was then increased to about 190° C. and the reaction mixture was stirred with $N_2$ distillation for about 1 hour after reaching this temperature. The nitrogen inlet tube was then lowered so as to be below the surface of the stirring 190° C. reaction mixture and the $N_2$ allowed to distill all un-reacted volatiles out of the flask for about 1 hour. The mixture was poured into aluminum pans and allowed to cool. The viscosity of the solid di-amide was about 26.5 cps as measured by a Ferranti-Shirley cone-plate viscometer at about 135° C.

The di-amide of Example 17 has the following formula:

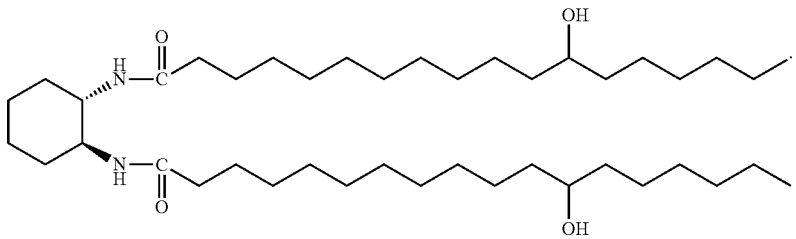

Example 18

About 50 g of aleuritic acid (available from Sabinsa Corp) was added to a 100 mL 1-necked 45/50 round bottom tube, with condenser and $N_2$ blowing through top of condenser, and with Teflon coated magnet. The reaction flask was placed in about a 130° C. oil bath and stirring was initiated. After about 30 minutes, about 9.5 grams of trans-1,2-diaminocyclohexane (available from Aldrich Chemical Company) was added. The temperature of the oil bath was increased to about 150° C. and stirred at this temperature for 1.5 hours. The condenser was then replaced with a distillation setup and a $N_2$ stream was introduced where the thermometer would be placed in the distillation head. The $N_2$ was distilled off the water while the reaction mixture was stirred at about 150° C. for about an additional 2 hours. The oil bath temperature controller was then increased to about 190° C. and the reaction mixture was stirred with $N_2$ distillation for about 1 hour after reaching this temperature. The nitrogen inlet tube was then removed and a vacuum introduced to distill all un-reacted volatiles out of the flask for about 1 hour. The mixture was poured into aluminum pans and allowed to cool. The viscosity of the solid di-amide was about 53.5 cps as measured by a Ferranti-Shirley cone-plate viscometer at about 135° C.

The di-amide of Example 18 has the following formula:

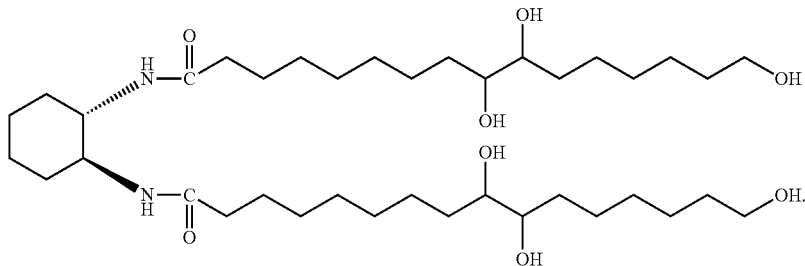

Characterization of Di-amides Derived from Hydroxyl Containing Carboxylic Acids

The melt viscosities at about 140° C. were about 24 cps for the di-amide in Example 17 based on 12-hydroxystearic acid, and about 45 cps for the one in Example 18 based on aleuritic acid.

The use of OH-containing acids lead to materials that are virtually amorphous at about room temperature, approximately 25° C. The only proof of the slight crystallization was seen in the storage modulus G' below about 70° C. for the resin of Example 18. Since these materials are amides, they are miscible with the other ink components. At the same time, they contribute to the hydrophilicity of the ink leading to an improved adhesion to paper and writability on the ink layer. G' is defined as the part of the shear stress that is in phase with the shear strain divided by the strain under sinusoidal deformation (elastic component).

Derived from Straight Chained Carboxylic Acids

Example 19

About 60 g of UNICID 700 (available from Baker Petrolite) and a Teflon coated magnet were added to a 100 mL 45/50 1-necked round bottom tube. A 45/50 4-neck adaptor was then attached to the 45/50 tube. A condenser was placed in the middle neck, a $N_2$ inlet was placed in one of the necks and a glass stopper was placed in each of the other 2 necks. The reaction flask was placed in about a 120° C. oil bath and stirring was initiated. After about 1 hour, about 3.8 grams of trans-1,2-diaminocyclohexane (available from Aldrich Chemical Company) was added through one of the necks and the stopper was replaced. The reaction mixture was stirred for about 1 hour at a temperature of about 120° C. The oil bath temperature controller was then increased to a temperature of about 190° C. and the reaction mixture was stirred for about 4 hours after reaching this temperature. The product was then poured into aluminum tins. The viscosity of the solid product was about 27 cps as measured by a Ferranti-Shirley cone-plate viscometer at a temperature of about 135° C.

The di-amide of Example 19 has the following formula:

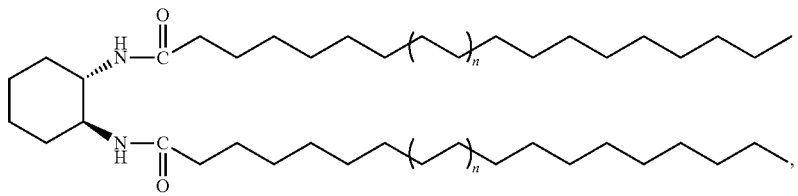

where n is 16.

Example 20

About 55 g of UNICID 550 (available from Baker Petrolite) and a Teflon coated magnet were added to a 100 mL 45/50 1-necked round bottom tube. A 45/50 4-neck adaptor was then attached to the 45/50 tube. A condenser was placed in the middle neck, a $N_2$ inlet was placed in one of the necks and a glass stopper was placed in each of the other 2 necks. The reaction flask was placed in about a 120° C. oil bath and stirring was initiated. After about 1 hour, about 4.1 grams of trans-1,2-diaminocyclohexane (available from Aldrich Chemical Company) was added through one of the necks and the stopper was replaced. The reaction mixture was stirred for about 1 hour at a temperature of about 120° C. The oil bath temperature controller was then increased to a temperature of about 190° C. and the reaction mixture was stirred for about 4 hours after reaching this temperature. The product was then poured into aluminum tins. The viscosity of the solid product was about 30 cps as measured by a Ferranti-Shirley cone-plate viscometer at a temperature of about 135° C.

The di-amide of Example 20 has the following formula:

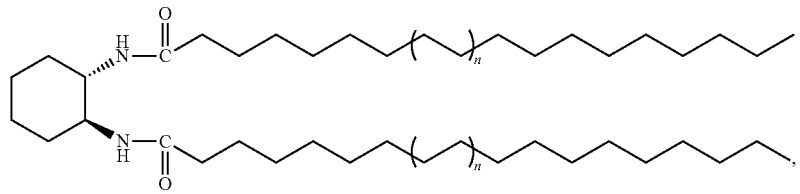

where n is 11.

Example 21

About 55 g of UNICID 425 (available from Baker Petrolite) and a Teflon coated magnet were added to a 100 mL 45/50 1-necked round bottom tube. A 45/50 4-neck adaptor was then attached to the 45/50 tube. A condenser was placed in the middle neck, a $N_2$ inlet was placed in one of the necks and a glass stopper was placed in each of the other 2 necks. The reaction flask was placed in about a 120° C. oil bath and stirring was initiated. After about 1 hour, about 5.3 grams of trans-1,2-diaminocyclohexane (available from Aldrich Chemical Company) was added through one of the necks and the stopper replaced. The reaction mixture was stirred for about 1 hour at a temperature of about 120° C. The oil bath temperature controller was then increased to a temperature of about 190° C. and the reaction mixture stirred for about 4 hours after reaching this temperature. The product was then poured into aluminum tins. The viscosity of the solid product was about 16.5 cps as measured by a Ferranti-Shirley cone-plate viscometer at a temperature of about 135° C.

The di-amide of Example 21 has the following formula:

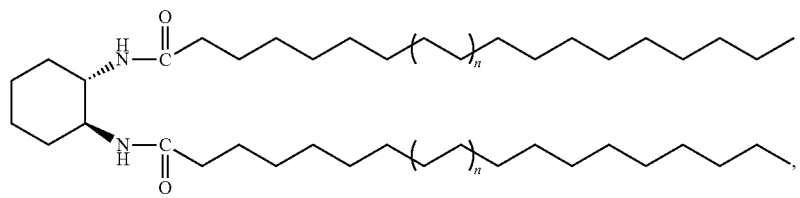

where n is 6.

Characterization of Di-amides Derived from Straight Chained Carboxylic Acids

The rheological measurements of Examples 19 through 21 were performed on a RFS3 Fluids Rheometer in the dynamic mode, using the 50 mm cone and a gap of 53 microns. The test performed was a temperature step sweep from about 140° C. to about 90° C. at a constant frequency of about 1 Hz. From about 140° C. to a temperature slightly above the onset of crystallization temperature, 5° C. decrements were used with an equilibration time of about 180 seconds at each temperature, followed by about 2° C. steps to about 90° C. at about 120 seconds intervals to determine the crystallization transition more accurately. Upon heating, 5° C. steps were used to obtain a temperature of about 140° C. to determine the temperature when there is a complete re-melting of the crystalline structure.

The viscosity at about 140° C. and the onset of crystallization temperatures are a function of the chain length of the starting acid used in the reaction. Due to their molecular conformation and possibly their ability to form hydrogen bonds, the di-amide materials of Examples 19-21 have a relatively high onset of crystallization temperature of over 110° C. However, due to their hardness, this class of materials may be used as ink vehicle components to improve ink robustness.

Examples Tetra-Amides

Derived from Straight Chained Carboxylic Acids

Example 22

About 511.8 g of UNICID 700 (available from Baker Petrolite) and about 158.8 grams of PRIPOL 1006 Dimer Acid (available from Uniqema) were added to a 4 necked 1 L kettle having heating mantle, nitrogen flow, distillation arm, mechanical Tru-Bore Stirrer, and thermocouple running to a temperature controller unit available from Watlow. The temperature was set at about 120° C. and heated. After the temperature had reached about 130° C. and all solids were molten, the stirrer was turned on and the temperature was dropped to about 120° C. The addition of about 56.5 grams of trans-1,2-diaminocyclohexane (available from Aldrich) was initiated through a 250 mL addition funnel. Addition was completed in about 3 minutes. The temperature was set at about 180° C. and the mixture was heated while being stirred for about 5 hours. The mixture was poured into an aluminum foil pan and allowed to cool. The viscosity of the tan waxy solid was about 70.0 cps as measured by a Ferranti-Shirley cone-plate viscometer at a temperature of about 135° C.

The tetra-amide of Example 22 has the following formula:

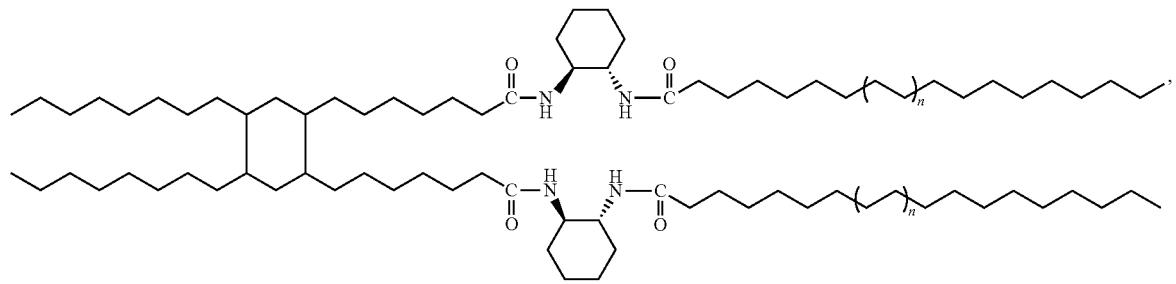

where n is 16.

Example 23

About 404.4 g UNICID 550 (available from Baker Petrolite) and about 158.5 grams of PRIPOL 1006 Dimer Acid (available from Uniqema) were added to a 4 necked 1 L kettle having a heating mantle, nitrogen flow, distillation arm, mechanical Tru-Bore Stirrer, and thermocouple running to a temperature controller unit available from Watlow. The temperature was set at about 120° C. and heated. After the temperature had reached about 130° C. and all solids were molten, the stirrer was turned on and the temperature dropped to about 120° C. The addition of about 56.5 grams of trans-1,2-diaminocyclohexane (available from Aldrich) was initiated through a 250 mL addition funnel. Addition was completed in about 3 minutes. The temperature was set at about 180° C. and the mixture was allowed to heat while being stirred for about 5 hours. The mixture was poured into an aluminum foil pan and allowed to cool. The viscosity of the tan waxy solid was about 76.5 cps as measured by a Ferranti-Shirley cone-plate viscometer at a temperature of about 135° C.

The tetra-amide of Example 23 has the following formula:

(available from Cognis) were added to a 1000 mL 3-necked round bottom flask having a condenser in the middle neck, a glass stopper in each of the other 2 outside necks, $N_2$ blowing through top of condenser and a Teflon coated magnet. The reaction flask was placed in about a 130° C. oil bath until the contents were molten (this took about 1 hour) and then stirring was initiated. About 40.1 g of trans-1,2-diaminocyclohexane (available from Aldrich Chemical Company) was added through one of the side arms. The oil bath temperature controller was then increased to about 150° C. and the reaction mixture was stirred for about 1 hour after reaching this temperature. The condenser was then replaced with a glass stopper (in the middle neck), a distillation setup was attached to one of the outside necks, and a $N_2$ stream attached to the other neck. The $N_2$ was distilled off the water while the reaction mixture was stirred at about 150° C. for about an additional 2 hours. The oil bath temperature controller was then increased to about 190° C. and the reaction mixture was stirred for about 1 hour, with the $N_2$ distillation setup after reaching this temperature. The reaction product was then

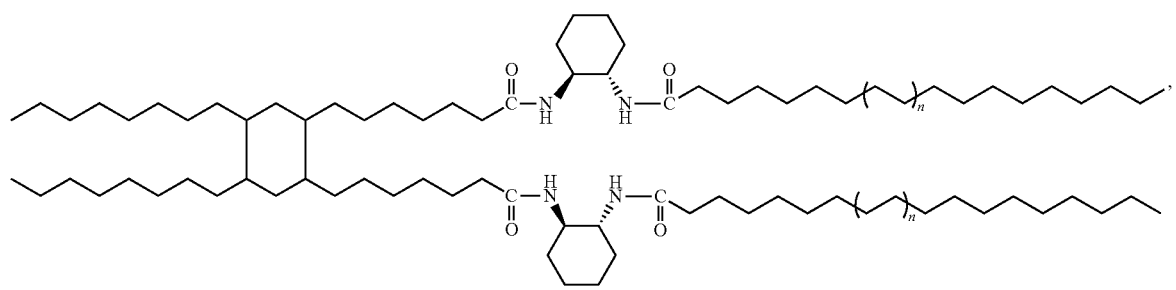

where n is 11.

Example 24

About 208.1 g of UNICID 550 (available from Baker Petrolite) and about 100 g of EMPOL 1008 Dimer Acid poured into aluminum tins and allowed to solidify. The viscosity of the viscous liquid was about 74.0 cps as measured by a Ferranti-Shirley cone-plate viscometer at a temperature of about 135° C.

The tetra-amide of Example 24 has the following formula:

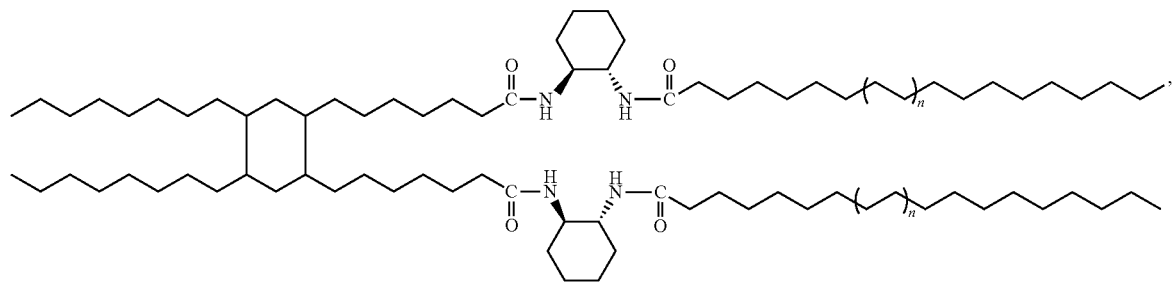

where n is 11.

Example 25

About 301.8 g of UNICID 425 (available Baker Petrolite) and about 158.8 g of PRIPOL 1006 Dimer Acid (available from Uniqema) were added to a 4 necked 1 L kettle having a heating mantle, nitrogen flow, distillation arm, mechanical Tru-Bore Stirrer, and a thermocouple running to a temperature controller unit available from Watlow. The temperature was set at about 120° C. and allowed to heat. After the temperature had reached about 130° C. and all solids were molten, the stirrer was turned on and the temperature was dropped to about 120° C. The addition of about 57 grams of trans-1, 2-diaminocyclohexane (available from Aldrich) was initiated through a 250 mL addition funnel. Addition was completed in about 3 minutes. The temperature was set at about 180° C. and the mixture was allowed to heat while being stirred for about 5 hours. The mixture was poured into an aluminum foil pan and allowed to cool. The viscosity of the tan waxy solid was about 88.7 cps as measured by a Ferranti-Shirley cone-plate viscometer at a temperature of about 135° C.

The tetra-amide of Example 25 has the following formula:

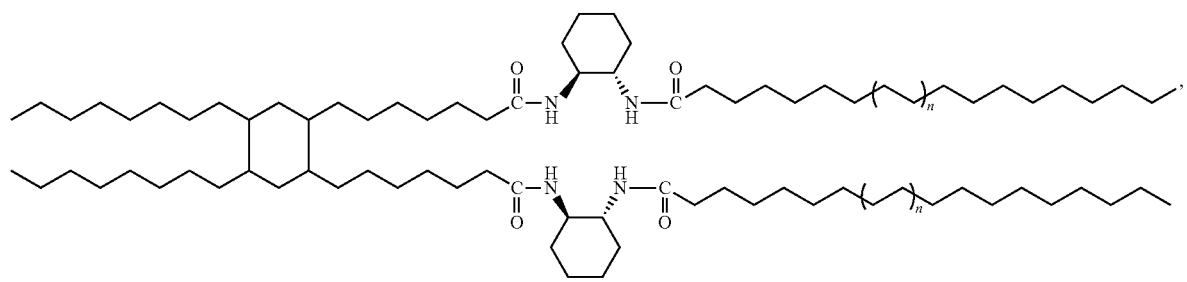

where n is 6.

Example 26

About 389.6 g of UNICID 350 (available Baker Petrolite) and about 250.0 g of PRIPOL 1006 Dimer Acid (available from Uniqema) were added to a 4 necked 1 L kettle having a heating mantle, nitrogen flow, distillation arm, mechanical Tru-Bore Stirrer, and a thermocouple running to a temperature controller unit available from Watlow. The temperature was set at about 120° C. and allowed to heat. After the temperature had reached about 130° C. and all solids were molten, the stirrer was turned on and the temperature was dropped to about 120° C. The addition of about 99.1 grams of trans-1,2-diaminocyclohexane (available from Aldrich) was initiated through a 250 mL addition funnel. Addition was completed in about 3 minutes. The temperature was set at about 180° C. and the mixture was allowed to heat while being stirred for about 5 hours. The mixture was poured into an aluminum foil pan and allowed to cool.

The tetra-amide of Example 26 has the following formula:

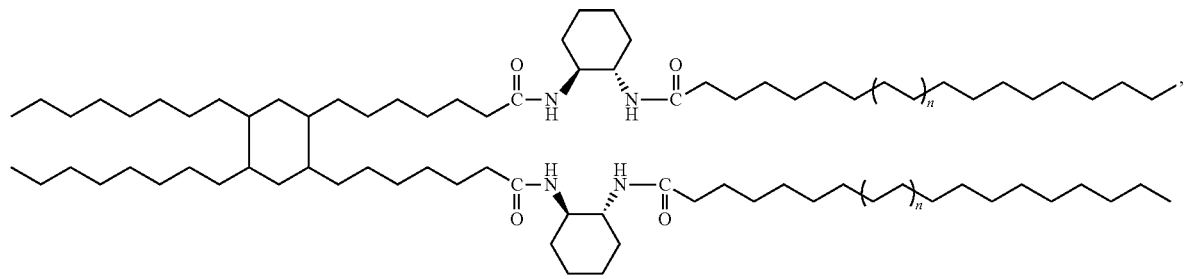

where n is 3.

Example 27

About 176.5 g of behenic acid (available as Prifrac 2989 from Uniqema) and about 158.8 grams of PRIPOL 1006 Dimer Acid (available from Uniqema) were added to a 4 necked 1 L kettle having a heating mantle, nitrogen flow, distillation arm, mechanical Tru-Bore Stirrer, and a thermocouple running to a temperature controller unit available from Watlow. The temperature was set at about 120° C. and allowed to heat. After the temperature had reached about 130° C. and all solids were molten, the stirrer was turned on and the temperature was dropped to about 120° C. The addition of about 57 g of trans-1,2-diaminocyclohexane (available from Aldrich) was initiated through a 250 mL addition funnel. Addition was completed in about 3 minutes. The temperature was set at about 180° C. and the mixture was allowed to heat while being stirred for about 5 hours. The mixture was poured into an aluminum foil pan and allowed to cool. The viscosity of the tan waxy solid was about, 950 cps as measured by a Ferranti-Shirley cone-plate viscometer at a temperature of about 135° C.

The tetra-amide of Example 26 has the following formula:

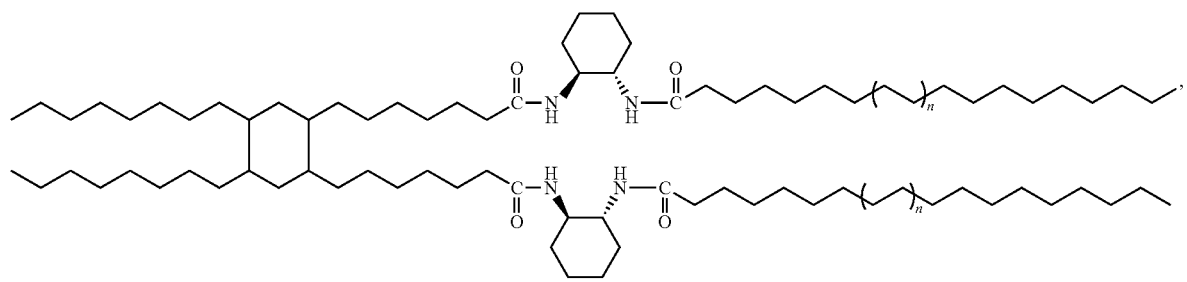

where n is 3.

Example 28

About 145.4 g of stearic acid (available from Aldrich Chemical Corp) and about 158.5 grams of PRIPOL 1006 Dimer Acid (available from Uniqema) were added to a 4 necked 1 L kettle having a heating mantle, nitrogen flow, distillation arm, mechanical Tru-Bore Stirrer, and a thermocouple running to a temperature controller unit available from Watlow. The temperature was set at about 120° C. and allowed to heat. After the temperature had reached about 130° C. and all solids were molten, the stirrer was turned on and the temperature was dropped to about 120° C. The addition of about 57 g of trans-1,2-diaminocyclohexane (available from Aldrich) was initiated through a 250 mL addition funnel. Addition was completed in about 3 minutes. The temperature was set at about 180° C. and the mixture was allowed to heat while being stirred for about 5 hours. The mixture was poured into an aluminum foil pan and allowed to cool.

The tetra-amide of Example 28 has the following formula:

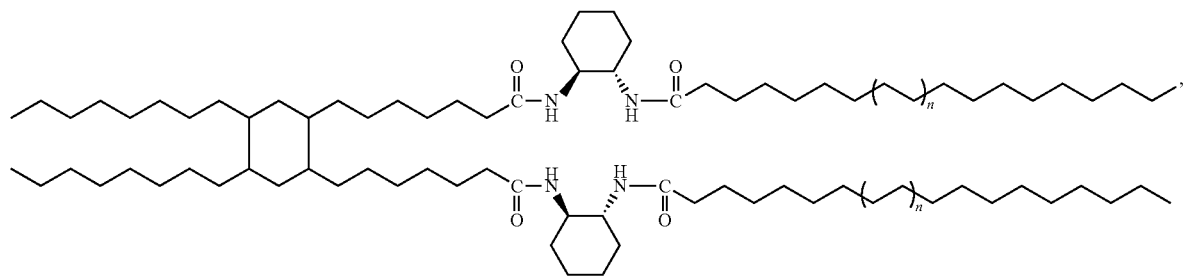

where n is 0.

Characterization of Tetra-amides Derived from Straight Chained Carboxylic Acids

These tetra-amide materials cover an entire range of properties, depending on the chain length of the straight chain carboxylic acid used, as seen in Table 2 below.

| Example | Tetra-amide Derived From a Straight Chained Carboxylic Acid | Viscosity@ 140° C. (cps) | Viscosity@ 110° C. (cps) | Onset of crystallization (° C.) - Rheology | Heat of Fusion (J/g) |
|---|---|---|---|---|---|
| 22 | Unicid 700 | 59.6 | 186 | 96 | 154 |
| 23 | Unicid 550 | 61.3 | 234.7 | 92 | 133 |
| 24 | Unicid 550 | 67.8 | 309.1 | 103 | 128 |
| 25 | Unicid 425 | 70.3 | 308.7 | 94 | 91.3 |
| 26 | Unicid 350 | 77.5 | 372.3 | 98 | 19.3 |
| 27 | Behenic Acid | 127.3 | 1930.5 | 115 | 19.3 |
| 28 | Stearic Acid | 172.3 | 240000 | 120 | 14.9 |

The UNICID 550 of Examples 23 and 24 provide slightly different results because of stoichiometric differences between the two UNICID's obtained from different manufacturers.

All the tetra-amide materials set forth in Table 2 above are hard at about room temperature, approximately 25° C. The tetra-amides with longer chains are highly crystalline, have a lower melt viscosity and are more opaque. The tetra-amides with shorter chains are more amorphous, have higher viscosities and at the same time have improved transparency.

Derived from Hydroxyl Containing Carboxylic Acids

Example 29

About 102 grams of 12-hydroxystearic acid (available from Caschem) and about 105.5 g PRIPOL 1006 Dimer Acid were added to a 4 necked 1 L kettle having a heating mantle, nitrogen flow, distillation arm, mechanical Tru-Bore Stirrer, and a thermocouple running to a temperature controller unit. The temperature was set at about 120° C. and allowed to heat. After about 50 minutes, the temperature had reached about 133° C. and all contents were molten. The stirrer was turned on. The temperature was set at about 110° C. and the mantle was lowered to facilitate cooling. When the temperature had reached about 106° C. the mantle was raised and about 57 grams of trans-1,2-diaminocyclohexane (available from Aldrich) was added through a 250 mL addition funnel. The addition was completed in about 3 minutes. The temperature was set at about 180° C. and the mixture was allowed to heat while being stirred for about 5 hours. The mixture was poured into an aluminum foil pan and allowed to cool and solidify.

The tetra-amide of Example 29 has the following formula:

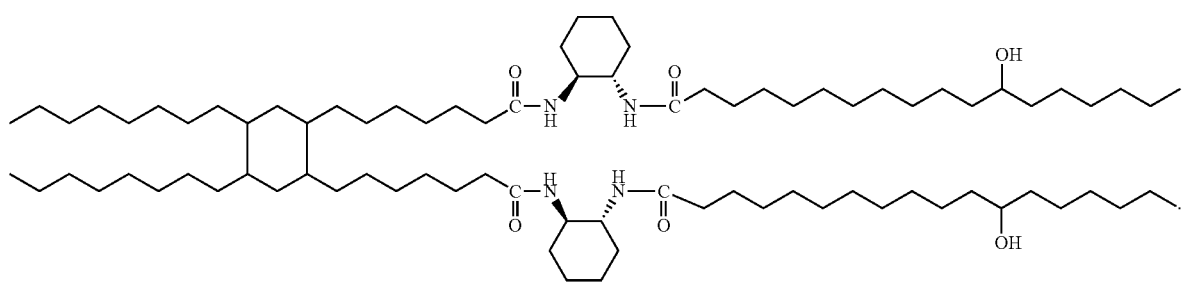

Example 30

About 166 g of 12-hydroxystearic acid (available from Caschem) and about 150 g of EMPOL 1008 Dimer Acid (available from Cognis) were added to a 1000 mL 3-necked round bottom flask having a condenser in the middle neck, a glass stopper in each of the other 2 outside necks, $N_2$ blowing through the top of the condenser and a Teflon coated magnet. The reaction flask was placed in about a 120° C. oil bath and stirring was initiated. After about 5 minutes, about 60 g of trans-1,2-diaminocyclohexane (available from Aldrich Chemical Company) was added through one of the side arms. The reaction mixture stirred for about 10 minutes at about 120° C. The oil bath temperature controller was then increased to a temperature of about 150° C. and the reaction mixture was stirred for about 1 hour after reaching this temperature. The condenser was then replaced with a glass stopper (in the middle neck), a distillation setup was attached to one of the outside necks and a $N_2$ stream was attached to the other neck. The $N_2$ was distilled off the water while the reaction mixture was stirred at about 150° C. for about an additional 2 hours. The oil bath temperature controller was then increased to about 190° C. and the reaction mixture stirred for about 1 hour with $N_2$ stream. After reaching this temperature, the reaction product was then poured into aluminum tins and allowed to solidify. The viscosity of the viscous liquid was about 162.9 cps as measured by a Ferranti-Shirley cone-plate viscometer at about 135° C.

The tetra-amide of Example 30 has the following formula:

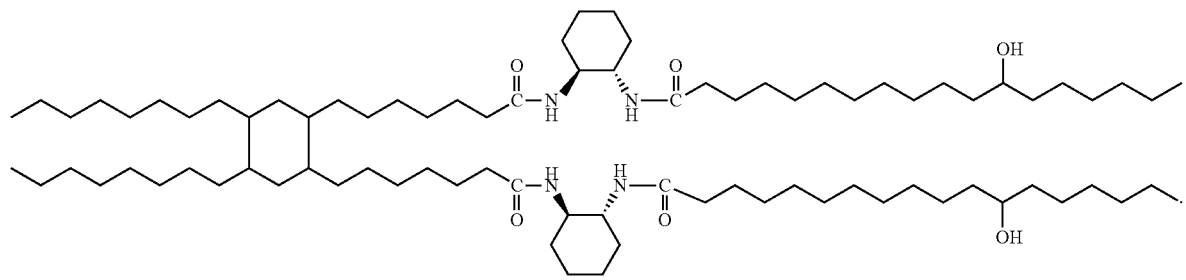

Example 31

About 31.7 g of aleuritic acid (available from Sabinsa Corp) and about 30 g of Empol 1008 Dimer Acid (available from Cognis) were added to a 100 mL 1-necked 45/50 round bottom tube having a condenser, $N_2$ blowing through the top of the condenser and a Teflon coated magnet. The reaction flask was placed in about a 130° C. oil bath and stirring was initiated. After about 30 minutes, about 12 g of trans-1,2-diaminocyclohexane (available from Aldrich Chemical Company) was added. The temperature of the oil bath was increased to about 150° C. and stirred at this temperature for about 1.5 hours. The condenser was then replaced with a distillation setup and $N_2$ stream was introduced where the thermometer would be placed in the distillation head. The $N_2$ was distilled off the water while the reaction mixture was stirred at about 150° C. for about an additional 2 hours. The oil bath temperature controller was then increased to about 190° C. and the reaction mixture was stirred with $N_2$ distillation for about 1 hour after reaching this temperature. The nitrogen inlet tube was then removed and a vacuum was introduced to distill all unreacted volatiles out of the flask for about 1 hour. The mixture was poured into aluminum pans and allowed to cool. The viscosity of the solid di-amide was about 663.65 cps as measured by a Ferranti-Shirley cone-plate viscometer at about 135° C.

The tetra-amide of Example 31 has the following formula:

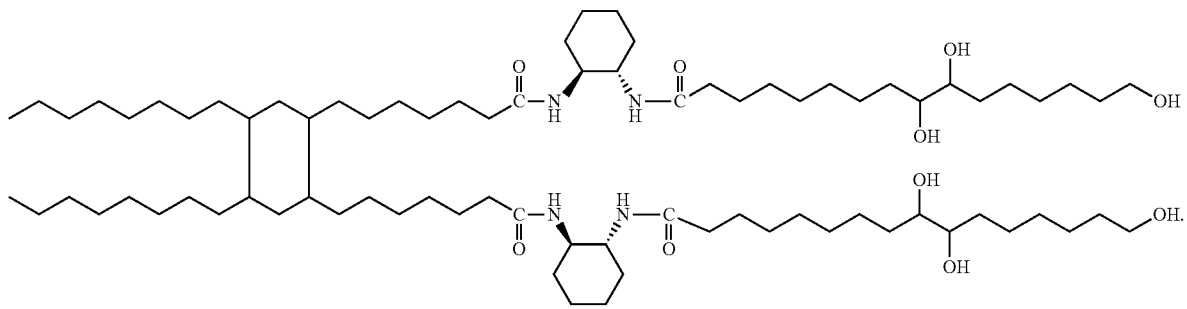

Characterization of Tetra-amides Derived from Hydroxyl Containing Carboxylic Acids The properties of the materials that are described in the preceding examples depend on the type of hydroxyl containing carboxylic acids used. In Examples 27 and 28, 12-hydroxystearic acid was employed. Both Examples 26 and 27 have identical thermal and rheological properties. Their viscosities were about 160 cps at a temperature of about 140° C., and had an onset of crystallization temperature of about 80° C. Both Examples 26 and 27 were transparent at about room temperature, approximately 25° C.

The molecular conformation of the aleuritic acid used Example 28 inhibited the crystallization of the material. At about 140° C., it had a viscosity of about 650 cps. This particular tetra-amide of Example 28 was mostly amorphous and did not show any crystallization behavior at a temperature as low as about 60° C. This material was very hard and transparent at about room temperature, approximately 25° C., and could be used as a replacement for the KE100 resin, which is much more brittle and has a viscosity of about 4000 cps at a temperature of about 140° C.

Derived from Branched Carboxylic Acids

Example 32

About 25 g PRIPOL 1006 dimer acid (available from Uniqema) and about 24.6 g of isostearic acid (available as Prisorine 3505 from Uniqema) were added to a 100 mL 45/50 1-necked round bottom tube having a Teflon coated magnet. A 45/50 4-neck adaptor was then attached to the 45/50 tube. A condenser was placed in the middle neck, a $N_2$ inlet was placed in one of the necks and a glass stopper was placed in each of the other 2 necks. The reaction flask was placed in about a 120° C. oil bath and stirring was initiated. After about 1 hour, about 9.9 g of trans-1,2-diaminocyclohexane (available from Aldrich Chemical Company) was added through one of the necks and the stopper was replaced. The reaction mixture was stirred for about 1 hour at a temperature of about 120° C. The oil bath temperature controller was then increased to about 190° C. and the reaction mixture was stirred for about 4 hours after reaching this temperature. The product was then poured into aluminum tins. The viscosity of the solid product was about 238.5 cps as measured by a Ferranti-Shirley cone-plate viscometer at a temperature of about 135° C.

The tetra-amide of Example 32 has the following formula:

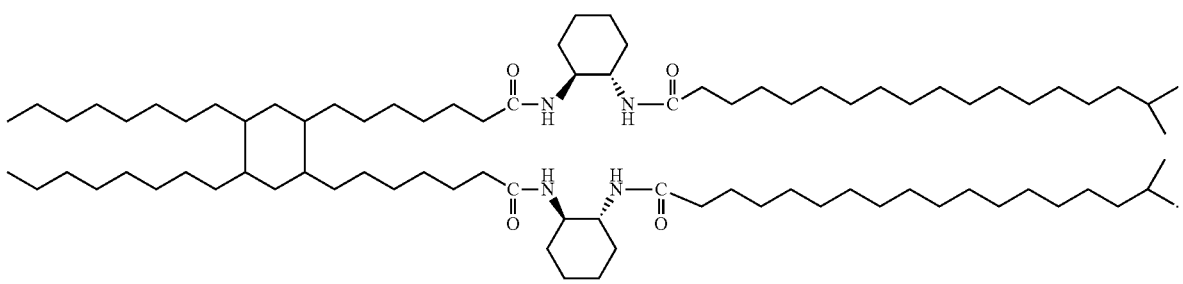

Example 33

About 152.4 g isostearic acid (available as Prisorine 3505 from Uniqema) and about 150 g EMPOL 1008 Dimer Acid (available from Cognis) were added to a 1000 mL 3-necked round bottom flask having a condenser in the middle neck, a glass stopper in each of the other 2 outside necks, $N_2$ blowing through the top of the condenser and a Teflon coated magnet. The reaction flask was placed in about a 120° C. oil bath and stirring was initiated. After about 5 minutes, about 60 g of trans-1,2-diaminocyclohexane (available from Aldrich Chemical Company) was added through one of the side arms. The reaction mixture was stirred for about 10 minutes at a temperature of about 120° C. The oil bath temperature controller was then increased to about 190° C. and the reaction mixture was stirred for about 1 hour after reaching this temperature. The condenser was then replaced with a glass stopper (in the middle neck), a distillation setup was attached to one of the outside necks and a $N_2$ stream was attached to the other neck. The $N_2$ was distilled off the water while the reaction mixture was stirred at about 190° C. for about an additional 2 hours. The reaction product was then poured into aluminum tins and allowed to solidify. The viscosity of the viscous liquid was about 229.9 cps as measured by a Ferranti-Shirley cone-plate viscometer at a temperature of about 135° C.

The tetra-amide of Example 33 has the following formula:

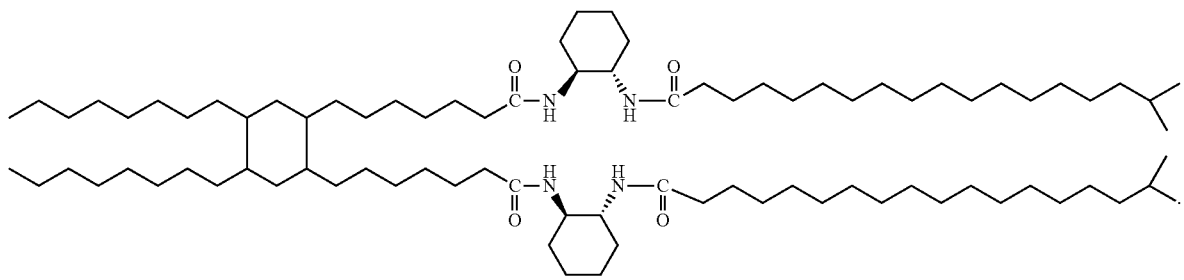

Example 34

About 25.6 g neooctanoic acid (available from Exxon Corp.) and about 50 g of EMPOL 1008 Dimer Acid (available from Cognis) were added to a 100 mL 1-necked 45/50 round bottom tube having condenser, $N_2$ blowing through the top of the condenser and a Teflon coated magnet. The reaction flask was placed in about a 130° C. oil bath and stirring was initiated. After about 30 minutes, about 20 g of trans-1,2-diaminocyclohexane (available from Aldrich Chemical Company) was added. The temperature of the oil bath was increased to about 150° C. and stirred at this temperature for about 1.5 hours. The condenser was then replaced with a distillation setup, and a $N_2$ stream was introduced where the thermometer would be placed in the distillation head. The $N_2$ was distilled off the water while the reaction mixture was stirred at a temperature of about 150° C. for about an additional 2 hours. The oil bath temperature controller was then increased to a temperature of about 190° C. and the reaction mixture was stirred with $N_2$ distillation for about 1 hour after reaching this temperature. The nitrogen inlet tube was then removed and a vacuum was introduced to distill all unreacted volatiles out of the flask for about 1 hour. The mixture was poured into aluminum pans and allowed to cool. The viscosity of the solid product was about 201.6 cps as measured by a Ferranti-Shirley cone-plate viscometer at a temperature of about 135° C.

The tetra-amide of Example 34 has the following formula:

Characterization of Tetra-amides Derived from Branched Carboxylic Acids

The use of 1,2-trans-diaminocyclohexane in the synthesis of tetra-amides leads to materials that have a higher amorphous component and as a result, they are hard and transparent. The use of branched carboxylic acids contributes even more to a disruption of the chain linearity and leads to materials that range from semicrystalline to amorphous. They have lower melting transitions as well as improved toughness. The materials from Examples 31 and 32 maintain their semicrystalline behavior, and have a viscosity of about 175 cps at a temperature of about 140° C., and a viscosity of about 1,200 cps at a temperature of about 110° C.

The neooctanoic acid used in Example 33 leads to a material with an even higher degree of amorphous content. The material of Example 33 is also hard at about room temperature, approximately 25° C., has a viscosity of about 410 cps at a temperature of about 110° C. and does not display any change in complex viscosity at a temperature as low as about 40° C.

For current ink formulations, these tetra-amide materials derived from branched carboxylic acids could completely or partially replace known tetra-amides, known triamides, and amorphous resins, such as KE100 resin.

It is believed that the lower degree of crystallinity of the this tetra-amide materials leads to improved miscibility with the other ink components, especially with amorphous resins, KE100 resin, as well as improved robustness.

Derived from a Dimer Acid, an Alkylene Diamine and a Carboxylic Acid

Example 35

About 100 g of EMPOL 1008 dimer acid (available from Uniqema) and about 101.5 g isostearic acid (available as Prisorine 3505 from Uniqema) were added to a 1000 mL 3-necked round bottom flask having a condenser in the middle neck, a glass stopper in each of the other 2 outside

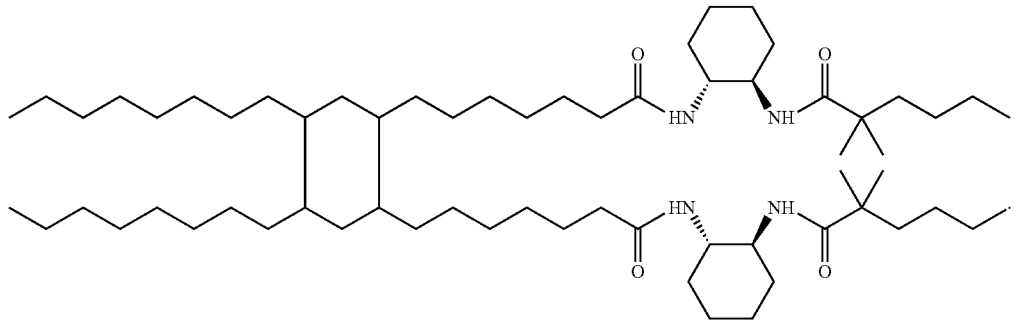

necks, $N_2$ blowing through top of condenser and Teflon coated magnet. The reaction flask was placed in about a 120° C. oil bath and stirring was initiated. After about 20 minutes, about 21.1 grams of ethylene diamine (available from Aldrich Chemical Company) was quickly added through one of the outside necks and the stopper was replaced. The oil bath temperature controller was then increased to about 180° C. and the reaction mixture was stirred for about 90 minutes after reaching this temperature. The condenser was then replaced with a glass stopper (in the middle neck), a distillation setup was attached to one of the outside necks and a $N_2$ stream was attached to the other neck. The $N_2$ was distilled off the water while the reaction mixture was stirred at about 180° C. for about 2 hours. The temperature was then increased to about 180° C., and the reaction mixture was stirred with the $N_2$ distillation. All unreacted volatiles were distilled out of the flask for about 1 hour. The product was poured into aluminum pans and allowed to cool. The viscosity of the solid tetra-amide was about 144 cps as measured by a Ferranti-Shirley cone-plate viscometer at about 110° C.

The tetra-amide of Example 35 has the following formula:

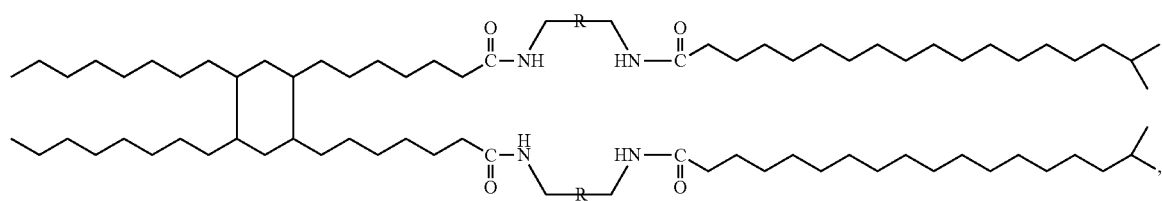

where R is ethylene.

Example 36

About 25.4 g of isostearic acid (available as PRISORINE 3505 from Uniqima) and about 25 g EMPOL 1008 Dimer Acid (available from Cognis) was added to a 100 mL 1-necked 45/50 round bottom tube having a condenser, $N_2$ blowing through the top of condenser and a Teflon coated magnet. The reaction flask was placed in about a 130° C. oil bath and stirring was initiated. After about 30 minutes, about 35.1 g of JEFFAMINE D-400 (available from the Texaco Chemical Company) was added. The temperature of the oil bath was increased to about 150° C. and stirred at this temperature for about 1.5 hours. The condenser was then replaced with a distillation setup and a $N_2$ stream was introduced where the thermometer would be placed in the distillation head. The $N_2$ was distilled off the water while the reaction mixture was stirred at about 150° C. for about an additional 2 hours. The oil bath temperature controller was then increased to about 190° C. and the reaction mixture was stirred with $N_2$ distillation for about 1 hour after reaching this temperature. The nitrogen inlet tube was then removed and a vacuum introduced to distill all unreacted volatiles out of the flask for about 1 hour. The mixture was poured into aluminum pans and allowed to cool.

The tetra-amide of Example 36 has the following formula:

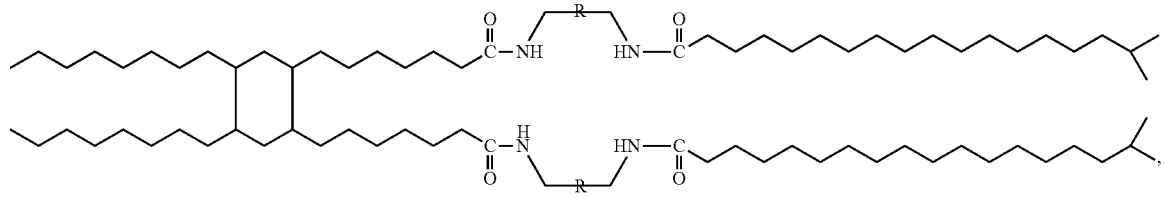

where R is

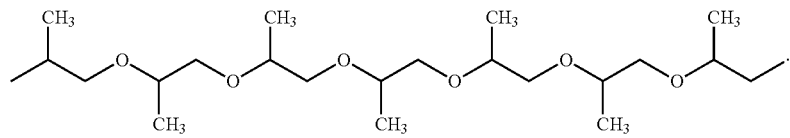

Characterization of Tetra-amide Derived from a Dimer Acid, and Alkylene Diamine and a Carboxylic Acid The change in the molecular conformation from straight chain stearic acid to non-linear isostearic acid leads to dramatically improved properties for ink applications. As a comparison, the properties of a known tetra-amide Comparative Example 1 is also presented in Table 3 below.

The presence of a carboxylic acid having seventeen carbon atoms in the synthesis of tetra-amides leads to materials with a higher concentration of amorphous content and a lower degree of crystallinity. The higher amorphous/crystalline ratio will also inhibit the growth of the crystalline fraction. These properties lead to the formation of a tough and transparent material. However, the molecular conformation of the isostearic acid based tetra-amide leads to a material with lower thermal transitions, the onset of crystallization occurring at a temperature of about 92° C. compared to 126° C. for Comparative Example 2.

TABLE 3

| Example | Tetra-amide-straight chain table | Viscosity @ 140° C. (cps) | Viscosity @ 110° C. (cps) | Onset of crystallization (° C.) - Rheology | Heat of Fusion (J/g) |
| --- | --- | --- | --- | --- | --- |
| Comparative Example 1 | Unicid 700 | 63.5 | 2052 | 118 | 141.5 |
| Comparative Example 2 | Stearic Acid | 87.3 | $5.9 \times 10^6$ | 126 | 47.3 |
| Example 35 | Isostearic Acid | 89.1 | 325 | 93 | 15.5 |

A tetra-amide derived from a dimer acid, and alkylene diamine and a carboxylic acid could be a replacement for the known tetra-amides and tri-amides, in addition to amorphous resins found in ink formulations, such as Resin 34 and KE100.

It is believed that the lower degree of crystallinity of the tetra-amides derived from a dimer acid, and alkylene diamine and a carboxylic acid will lead to improved miscibility with the other ink components, especially with the amorphous resins, such as Resin 34 or KE100, as well improved robustness of the ink.

The lower crystallization temperature of this tetra-amide (about 90° C.) is approximately the same as other crystalline ink components and therefore will contribute to a more homogeneous ink upon crystallization.

Ink Examples Including Amides Described Herein

Preparation of Ink Example A with Methyl Amide

An ink was prepared by melting, admixing, and filtering the following ingredients:
about 43.79 parts by weight polyethylene wax (PE 655®, obtained from Baker Petrolite) of the formula $CH_3(CH_2)_{50}CH_3$; about 19.38 parts by weight of a methyl amide based on Unicid 425 (obtained from Baker Petrolite and described in Example 4);

about 12.4 parts by weight tetra-amide resin obtained from the reaction of one equivalent of a C-36 dimer acid (obtained from Uniqema, New Castle, Del.) with two equivalents of ethylene diamine and UNICID® 700 (obtained from Baker Petrolite), a long chain hydrocarbon having a terminal carboxylic acid group, prepared as described in Example 1 of U.S. Pat. No. 6,174,937, which is incorporated by reference herein in its entirety;

about 1.83 parts by weight urethane resin obtained from the reaction of two equivalents of ABITOL® E hydroabietyl alcohol (obtained from Hercules Inc.) and one equivalent of isophorone diisocyanate, prepared as described in Example 1 of U.S. Pat. No. 5,782,966, which is incorporated by reference herein in its entirety;

about 6.48 parts by weight urethane resin that is the adduct of three equivalents of stearyl isocyanate and a glycerol-based alcohol, prepared as described in Example 4 of U.S. Pat. No. 6,309,453, which is incorporated by reference herein in its entirety;

about 0.2 parts by weight NAUGUARD® 445 antioxidant (obtained from Uniroyal Chemical Co.); and about 5.92 parts of a cyan dye as described in Example 4 of U.S. Pat. No. 5,919,839, which is incorporated by reference herein in its entirety.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 10.86 cps at about 140° C.

Preparation of Ink Example B with Methyl Amide

An ink was prepared by melting, admixing, and filtering the following ingredients:

about 43.79 parts by weight polyethylene wax (PE 655®, obtained from Baker Petrolite) of the formula $CH_3(CH_2)_{50}CH_3$;

about 19.38 parts by weight of an methyl amide based on UNICID® 350 (obtained from Baker Petrolite and described in Example 4);

about 12.4 parts by weight tetra-amide resin obtained from the reaction of one equivalent of a C-36 dimer acid (obtained from Uniqema, New Castle, Del.) with two equivalents of ethylene diamine and UNICID® 700 (obtained from Baker Petrolite), a long chain hydrocarbon having a terminal carboxylic acid group, prepared as described in Example 1 of U.S. Pat. No. 6,174,937;

about 11.83 parts by weight urethane resin obtained from the reaction of two equivalents of ABITOL® E hydroabietyl alcohol (obtained from Hercules Inc.) and one equivalent of isophorone diisocyanate, prepared as described in Example 1 of U.S. Pat. No. 5,782,966;

about 6.48 parts by weight urethane resin that is the adduct of three equivalents of stearyl isocyanate and a glycerol-based alcohol, prepared as described in Example 4 of U.S. Pat. No. 6,309,453;

about 0.2 parts by weight NAUGUARD® 445 antioxidant (obtained from Uniroyal Chemical;

about 5.92 parts of a cyan dye as described in example 4 of U.S. Pat. No. 5,919,839.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AD obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 10.47 cps at about 140° C.

Preparation of Ink Example C with Methyl Amide

An ink was prepared by melting, admixing, and filtering the following ingredients:
about 46.25 parts by weight polyethylene wax (PE 500®, obtained from Baker Petrolite) of the formula $CH_3(CH_2)_{50}CH_3$;

about 19.08 parts by weight of an methyl amide based on UNICID® 425 (obtained from Baker Petrolite) and described in Example 4);

about 17.13 parts by weight tri-amide resin obtained from the reaction of one equivalent of a Jeffamine available from Huntsman International LLC and 3 equivalents of a C-36 UNICIDS 550 (obtained from Baker Petrolite), a long chain hydrocarbon having a terminal carboxylic acid group, prepared as described in Example 1 of U.S. Pat. No. 6,174,937;

about 11.62 parts by weight KE100;

about 2.17 parts by weight urethane resin that is the adduct of three equivalents of stearyl isocyanate and a glycerol-based alcohol, prepared as described in Example 4 of U.S. Pat. No. 6,309,453;

about 0.2 parts by weight NAUGUARD® 445 antioxidant (obtained from Uniroyal Chemical Co.); and about 3.55 parts of a cyan dye as described in Examples 5-10 of U.S. Pat. No. 6,472,523, which is incorporated by reference herein in its entirety.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after 6 hours. The ink base was poured into molds containing about 31 grams of the colorless ink base and allowed to cool. The viscosity was about 10.85 cps and about 110° C.

Preparation of Ink Example D with Methyl Amide

An ink was prepared by melting, admixing, and filtering the following ingredients:
about 46.25 parts by weight polyethylene wax (PE 500®, obtained from Baker Petrolite) of the formula $CH_3(CH_2)_{50}CH_3$);

about 19.08 parts by weight of an methyl amide based on UNICID® 350 (obtained from Baker Petrolite) and described in Example 4);

about 17.13 parts by weight tri-amide resin obtained from the reaction of one equivqlent of a Jeffamine available from Huntsman International LLC and 3 equivalents of a C-36 UNICID® 550 (obtained from Baker Petrolite), a long chain hydrocarbon having a terminal carboxylic acid group, prepared as described in Example 2 of U.S. Pat. No. 6,860,930, which is incorporated by reference herein in its entirety;

about 11.62 parts by weight KE100;

about 2.17 parts by weight urethane resin that is the adduct of three equivalents of stearyl isocyanate and a glycerol-based alcohol, prepared as described in Example 4 of U.S. Pat. No. 6,309,453;

about 0.2 parts by weight NAUGUARD® 445 antioxidant (obtained from Uniroyal Chemical Co.); and about 3.55 parts of a cyan dye as described in Examples 5-10 of U.S. Pat. No. 6,472,523.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after 6 hours. The ink base was poured into molds containing about 31 grams of the colorless ink base and allowed to cool. The viscosity was about 10.52 cps at about 110° C.

Preparation of Example E with Di-Amide

An ink was prepared by melting, admixing, and filtering the following ingredients:

about 38.9 parts by weight polyethylene wax (PE 655®, obtained from Baker Petrolite) of the formula $CH_3(CH_2)_{50}CH_3$);

about 24.48 parts by weight of the iso-stearyl gel di-amide described in Example 13;

about 17.26 parts by weight tetra-amide resin obtained from the reaction of one equivalent of a C-36 dimer acid (obtained from Uniqema, New Castle, Del.) with two equivalents of ethylene diamine and UNICID® 700 (obtained from Baker Petrolite), a long chain hydrocarbon having a terminal carboxylic acid group, prepared as described in Example 1 of U.S. Pat. No. 6,174,937;

about 11.04 parts by weight of a parts by weight urethane resin obtained from the reaction of two equivalents of ABITOL® E hydroabietyl alcohol (obtained from Hercules Inc.) and one equivalent of isophorone diisocyanate, prepared as described in Example 1 of U.S. Pat. No. 5,782,966;

about 2.2 parts by weight urethane resin that is the adduct of three equivalents of stearyl isocyanate and a glycerol-based alcohol, prepared as described in Example 4 of U.S. Pat. No. 6,309,453;

about 0.20 parts by weight NAUGUARD® 445 antioxidant (obtained from Uniroyal Chemical Co.); and about 5.92 parts of a cyan dye as described in Example 4 of U.S. Pat. No. 5,919,839.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 10.82 cps at about 140° C.

Preparation of Example F with Di-Amide

An ink was prepared by melting, admixing, and filtering the following ingredients:
  about 42.16 parts by weight polyethylene wax (PE 500®, obtained from Baker Petrolite) of the formula $CH_3(CH_2)_{50}CH_3$);
  about 24.48 parts by weight of the iso-stearyl gel di-amide described in Example 13;
  about 16.26 parts by weight tri-amide resin obtained from the reaction of one equivqlent of a Jeffamine available from Huntsman International LLC and 3 equivalents of a C-36 UNICID® 550 (obtained from Baker Petrolite), a long chain hydrocarbon having a terminal carboxylic acid group, prepared as described in Example 1 of U.S. Pat. No. 6,174,937;
  about 11.15 parts by weight KE100;
  about 2.2 parts by weight urethane resin that is the adduct of three equivalents of stearyl isocyanate and a glycerol-based alcohol, prepared as described in Example 4 of U.S. Pat. No. 6,309,453;
  about 0.2 parts by weight NAUGUARD® 445 antioxidant (obtained from Uniroyal Chemical Co.); and
  about 3.55 parts of a cyan dye as described in Examples 5-10 of U.S. Pat. No. 6,472,523.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity was about 10.93 cps at about 110° C.

Preparation of Example G with Tetra-Amide

An ink was prepared by melting, admixing, and filtering the following ingredients:
  about 46.7 parts by weight polyethylene wax (PE 655®, obtained from Baker Petrolite) of the formula $CH_3(CH_2)_{50}CH_3$);
  about 17.42 parts by weight of the tetra-amide based on UNICID® 700 described in Example 22;
  about 12.76 parts by weight stearyl stearamide wax (KEMAMIDE® S-180, obtained from Crompton Corporation);
  about 12.0 parts by weight of a parts by weight urethane resin obtained from the reaction of two equivalents of ABITOL® E hydroabietyl alcohol (obtained from Hercules Inc.) and one equivalent of isophorone diisocyanate, prepared as described in Example 1 of U.S. Pat. No. 5,782,966;
  about 4.99 parts by weight urethane resin that is the adduct of three equivalents of stearyl isocyanate and a glycerol-based alcohol, prepared as described in Example 4 of U.S. Pat. No. 6,309,453;
  about 0.2 parts by weight NAUGUARD® 445 antioxidant (obtained from Uniroyal Chemical Co.); and
  about 5.92 parts of a cyan dye as described in Example 4 of U.S. Pat. No. 5,919,839.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 9.62 cps at about 140° C.

Preparation of Example H with Tetra-Amide

An ink was prepared by melting, admixing, and filtering the following ingredients:
  about 46.7 parts by weight polyethylene wax (PE 655®, obtained from Baker Petrolite) of the formula $CH_3(CH_2)_{50}CH_3$);
  about 17.42 parts by weight of the gel tetra-amide based on UNICID® 550 described in Example 23;

about 12.76 parts by weight stearyl stearamide wax (KE-MAMIDE® S-180, obtained from Crompton Corporation);

about 12.0 parts by weight of a parts by weight urethane resin obtained from the reaction of two equivalents of ABITOL® E hydroabietyl alcohol (obtained from Hercules Inc.) and one equivalent of isophorone diisocyanate, prepared as described in Example 1 of U.S. Pat. No. 5,782,966;

about 4.99 parts by weight urethane resin that is the adduct of three equivalents of stearyl isocyanate and a glycerol-based alcohol, prepared as described in Example 4 of U.S. Pat. No. 6,309,453;

about 0.2 parts by weight NAUGUARD® 445 antioxidant (obtained from Uniroyal Chemical Co.); and about 5.92 parts of a cyan dye as described in Example 4 of U.S. Pat. No. 5,919,839.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 9.98 cps at about 140° C.

Preparation of Example I with Tetra-Amide

An ink was prepared by melting, admixing, and filtering the following ingredients:

about 46.7 parts by weight polyethylene wax (PE 655®, obtained from Baker Petrolite) of the formula $CH_3(CH_2)_{50}CH_3$);

about 17.42 parts by weight of the gel tetra-amide based on UNICID® 425 described in Example 23;

about 12.76 parts by weight stearyl stearamide wax (KE-MAMIDE® S-180, obtained from Crompton Corporation);

about 12 parts by weight of a parts by weight urethane resin obtained from the reaction of two equivalents of ABI-TOL® E hydroabietyl alcohol (obtained from Hercules Inc.) and one equivalent of isophorone diisocyanate, prepared as described in Example 1 of U.S. Pat. No. 5,782,966;

about 4.99 parts by weight urethane resin that is the adduct of three equivalents of stearyl isocyanate and a glycerol-based alcohol, prepared as described in Example 4 of U.S. Pat. No. 6,309,453;

about 0.2 parts by weight NAUGUARD® 445 antioxidant (obtained from Uniroyal Chemical Co.); and about 5.92 parts of a cyan dye as described in Example 4 of U.S. Pat. No. 5,919,839.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 10.26 cps at about 140° C.

Preparation of Example J with Tetra-Amide

An ink was prepared by melting, admixing, and filtering the following ingredients:

about 50.0 parts by weight polyethylene wax (PE 500®, obtained from Baker Petrolite) of the formula $CH_3(CH_2)_{50}CH_3$);

about 15.6 parts by weight stearyl stearamide wax (KE-MAMIDE® S-180, obtained from Crompton Corporation);

about 15.4 parts by weight tri-amide resin obtained from the reaction of one equivalent of a Jeffamine available from Huntsman International LLC and 3 equivalents of a C-36 UNICID® 550 (obtained from Baker Petrolite), a long chain hydrocarbon having a terminal carboxylic acid group, prepared as described in Example 1 of U.S. Pat. No. 6,174,937;

about 13.08 parts by weight of the gel tetra-amide based on UNICID® 700 described in Example 22;

about 2.17 parts by weight urethane resin that is the adduct of three equivalents of stearyl isocyanate and a glycerol-based alcohol, prepared as described in Example 4 of U.S. Pat. No. 6,309,453;

about 0.20 parts by weight NAUGUARD® 445 antioxidant (obtained from Uniroyal Chemical Co.); and about 3.55 parts of a cyan dye as described in Examples 5-10 of U.S. Pat. No. 6,472,523.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after 6 hours. The ink base was poured into molds containing about 31 grams of the colorless ink base and allowed to cool. The viscosity was about 11.5 cps at about 110° C.

Preparation of Example K with Tetra-Amide

An ink was prepared by melting, admixing, and filtering the following ingredients:

about 50.8 parts by weight polyethylene wax (PE 500®, obtained from Baker Petrolite) of the formula $CH_3(CH_2)_{50}CH_3$);

about 15.6 parts by weight stearyl stearamide wax (KE-MAMIDE® S-180, obtained from Crompton Corporation);

about 15.4 parts by weight tri-amide resin obtained from the reaction of one equivalent of a Jeffamine available from Huntsman International LLC and 3 equivalents of a C-36 UNICID® 550 (obtained from Baker Petrolite), a long chain hydrocarbon having a terminal carboxylic acid group, prepared as described in Example 1 of U.S. Pat. No. 6,174,937;

about 12.28 parts by weight of the gel tetra-amide based on UNICID® 550 described in Example 23;

about 2.17 parts by weight urethane resin that is the adduct of three equivalents of stearyl isocyanate and a glycerol-based alcohol, prepared as described in Example 4 of U.S. Pat. No. 6,309,453;

about 0.20 parts by weight NAUGUARD® 445 antioxidant (obtained from Uniroyal Chemical Co.); and about 3.55 parts of a cyan dye as described in Examples 5-10 of U.S. Pat. No. 6,472,523.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity was 10.86 cps at about 110° C.

Preparation of Example L with Tetra-Amide

An ink was prepared by melting, admixing, and filtering the following ingredients:

about 47.46 parts by weight polyethylene wax (PE 655®, obtained from Baker Petrolite) of the formula $CH_3(CH_2)_{50}CH_3$);

about 22.68 parts by weight of the gel tetra-amide based on hydroxystearic acid described in Example 28;

about 13.6 parts by weight stearyl stearamide wax (KEMAMIDE® S-180, obtained from Crompton Corporation);

about 6.14 parts by weight of a parts by weight urethane resin obtained from the reaction of two equivalents of ABITOL® E hydroabietyl alcohol (obtained from Hercules Inc.) and one equivalent of isophorone diisocyanate, prepared as described in Example 1 of U.S. Pat. No. 5,782,966;

about 4.0 parts by weight urethane resin that is the adduct of three equivalents of stearyl isocyanate and a glycerol-based alcohol, prepared as described in Example 4 of U.S. Pat. No. 6,309,453;

about 0.2 parts by weight NAUGUARD® 445 antioxidant (obtained from Uniroyal Chemical Co.); and about 5.92 parts of a cyan dye as described in Example 4 of U.S. Pat. No. 5,919,839.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 11.02 cps at about 140° C.

Preparation of Example M with Tetra-Amide

An ink was prepared by melting, admixing, and filtering the following ingredients:

about 50.0 parts by weight polyethylene wax (PE 500®, obtained from Baker Petrolite) of the formula $CH_3(CH_2)_{50}CH_3$);

about 28.85 parts by weight of the gel tetra-amide based on hydroxystearic acid described in Example 28;

about 15.4 parts by weight tri-amide resin obtained from the reaction of one equivalent of a Jeffamine available from Huntsman International LLC and 3 equivalents of a C-36 UNICID® 550 (obtained from Baker Petrolite), a long chain hydrocarbon having a terminal carboxylic acid group, prepared as described in Example 1 of U.S. Pat. No. 6,174,937;

about 2.0 parts by weight urethane resin that is the adduct of three equivalents of stearyl isocyanate and a glycerol-based alcohol, prepared as described in Example 4 of U.S. Pat. No. 6,309,453;

about 0.20 parts by weight NAUGUARD® 445 antioxidant (obtained from Uniroyal Chemical Co.); and about 3.55 parts of a cyan dye as described in Examples 5-10 of U.S. Pat. No. 6,472,523.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity was about 11.64 cps at about 110° C.

Preparation of Example N with Tetra-Amide

An ink was prepared by melting, admixing, and filtering the following ingredients:

about 48.86 parts by weight polyethylene wax (PE 655®, obtained from Baker Petrolite) of the formula $CH_3(CH_2)_{50}CH_3$);

about 27.64 parts by weight of the gel tetra-amide based on isostearic acid described in Example 30;

about 13.38 parts by weight stearyl stearamide wax (KEMAMIDE® S-180, obtained from Crompton Corporation);

about 4.0 parts by weight urethane resin that is the adduct of three equivalents of stearyl isocyanate and a glycerol-based alcohol, prepared as described in Example 4 of U.S. Pat. No. 6,309,453;

about 0.20 parts by weight NAUGUARD® 445 antioxidant (obtained from Uniroyal Chemical Co.); and
about 5.92 parts of a cyan dye as described in example 4 of U.S. Pat. No. 5,919,839.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity of the ink was about 11.02 cps at about 140° C.

Preparation of Example O with Tetra-Amide

An ink was prepared by melting, admixing, and filtering the following ingredients:
about 48.2 parts by weight polyethylene wax (PE 500®, obtained from Baker Petrolite) of the formula $CH_3(CH_2)_{50}CH_3$);
about 17.2 parts by weight stearyl stearamide wax (KEMAMIDE® S-180, obtained from Crompton Corporation);
about 15.4 parts by weight tri-amide resin obtained from the reaction of one equivalent of a Jeffamine available from Huntsman International LLC and 3 equivalents of a C-36 UNICID® 550 (obtained from Baker Petrolite), a long chain hydrocarbon having a terminal carboxylic acid group, prepared as described in Example 1 of U.S. Pat. No. 6,174,937;
about 13.45 parts by weight of the gel tetra-amide based on isostearic acid described in Example 30;
about 2 parts by weight urethane resin that is the adduct of three equivalents of stearyl isocyanate and a glycerol-based alcohol, prepared as described in Example 4 of U.S. Pat. No. 6,309,453;
about 0.2 parts by weight NAUGUARD® 445 antioxidant (obtained from Uniroyal Chemical Co.); and
about 3.55 parts of a cyan dye as described in Examples 5-10 of U.S. Pat. No. 6,472,523.

Thereafter, about 600 grams of the ink carrier components as listed above in the percentages as listed above were added to a 1 liter beaker and heated in an oven at about 135° C. until molten. Subsequently, the beaker was inserted into a heating mantle set to about 135° C. and the contents of the beaker were stirred for about 45 minutes. The resulting ink was then filtered through a combination of Whatman #3 and 0.2 micron NAE filters and placed in a Mott filter assembly. Filtration was supported by the addition of about 1 percent by weight FILTER-AID obtained from Fluka Chemika, Switzerland, and proceeded at a temperature of about 135° C. until complete after about 6 hours. The ink base was poured into molds containing about 31 grams of the colorless ink base and allowed to cool. The viscosity was about 12.14 cps at about 110° C.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. An ink composition comprising an ink vehicle and a colorant, wherein the ink vehicle comprises a compound having a formula of $R^1$—CONH—$R^2$ or $R^2$—CONH—$R^1$, wherein $R^2$ is $CH_3$ and $R^1$ is an alkyl group having from 3 carbon atoms to 200 carbon atoms, and wherein the alkyl group for $R^1$ includes at least one hydroxyl group substituent.

2. The ink composition according to claim 1, wherein the alkyl group for $R^1$ is a straight chain.

3. The ink composition according to claim 2, wherein the straight chain alkyl group includes at least one heteroatom in addition to the at least one hydroxyl group substituent.

4. The ink composition according to claim 1, wherein the alkyl group for $R^1$ is a branched chain alkyl group.

5. The ink composition according to claim 4, wherein the branched chain alkyl group includes at least one heteroatom in addition to the at least one hydroxyl group substituent.

6. The ink composition according to claim 1, wherein the compound is selected from the group consisting of

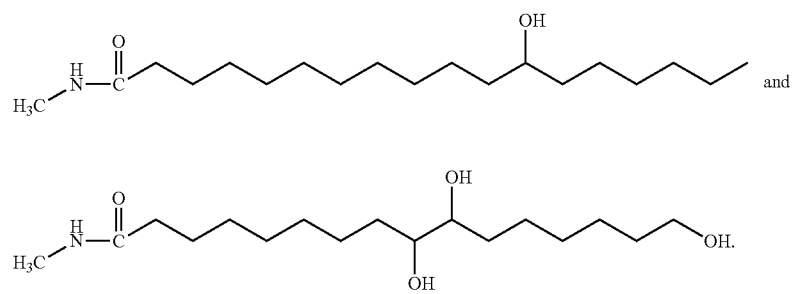

7. The ink composition according to claim 1, wherein the ink composition has a viscosity of from 18.5 cps to 5,000 cps at 140° C.

8. The phase change ink according to claim 7, wherein the compound is selected from the group consisting of

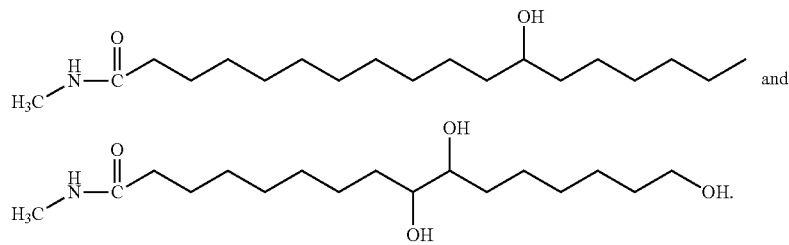
and

9. The ink composition according to claim 1, wherein the compound has a viscosity of from 18.5 cps to 1,000 cps at 140° C.

10. The ink composition according to claim 1, wherein the compound has a viscosity of from 18.5 cps to 500 cps at 140° C.

11. The ink composition according to claim 1, wherein the compound comprises from 5 weight percent to 100 weight percent of the ink vehicle.

12. The ink composition according to claim 1, wherein the ink vehicle further comprises a wax.

13. The ink composition according to claim 1, wherein the colorant is present in the ink in an amount from 0.5 to 75 percent by weight of the ink, and the colorant is a pigment, a dye, a mixture of pigments, a mixture of dyes or a mixture of pigments and dyes.

14. A phase change ink composition comprising an ink vehicle and a colorant, wherein the phase change ink is solid at temperatures of from 20° C. to 27° C. and exhibits a viscosity of from 1 to 20 centipoise (cP) at an elevated temperature at which the phase change ink is to be jetted, wherein the ink vehicle comprises a compound having a formula of $R^1$—CONH—$R^2$ or $R^2$—CONH—$R^1$, wherein $R^2$ is $CH_3$ and $R^1$ is an alkyl group having from 3 carbon atoms to 200 carbon atoms, and wherein the alkyl group for $R^1$ includes at least one hydroxyl group substituent.

15. The phase change ink according to claim 14, wherein the elevated temperature is a temperature within a range of from 50° C. to 150° C.

16. The phase change ink according to claim 14, wherein the ink vehicle further comprises a wax.

* * * * *